United States Patent
Capaldi et al.

(10) Patent No.: US 9,862,706 B2
(45) Date of Patent: Jan. 9, 2018

(54) COMPOUNDS

(71) Applicant: CHIESI FARMACEUTICI S.P.A., Parma (IT)

(72) Inventors: Carmelida Capaldi, Parma (IT); Elisabetta Armani, Parma (IT); Andrew Stephen Robert Jennings, Harlow (GB)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 15/606,064

(22) Filed: May 26, 2017

(65) Prior Publication Data

US 2017/0342056 A1 Nov. 30, 2017

(30) Foreign Application Priority Data

May 31, 2016 (EP) ..................................... 16172199

(51) Int. Cl.
| | | |
|---|---|---|
| *C07D 403/04* | (2006.01) | |
| *C07D 233/86* | (2006.01) | |
| *C07C 309/29* | (2006.01) | |
| *C07D 231/22* | (2006.01) | |

(52) U.S. Cl.
CPC .......... *C07D 403/04* (2013.01); *C07C 309/29* (2013.01); *C07D 231/22* (2013.01); *C07D 233/86* (2013.01)

(58) Field of Classification Search
CPC ................................................... C07D 403/04
See application file for complete search history.

(56) References Cited

U.S. PATENT DOCUMENTS

2014/0018345 A1 1/2014 Capaldi et al.
2016/0168101 A1* 6/2016 Armani ................ C07D 233/70
514/254.05

FOREIGN PATENT DOCUMENTS

| EP | 2 740 728 | 6/2014 |
| WO | 2015/124563 | 8/2015 |
| WO | 2016/096638 | 6/2016 |

OTHER PUBLICATIONS

European Search Report in Application No. 16172199.8 dated Aug. 2, 2016.
International Search Report in Application No. PCT/EP2017/062757 dated Jul. 13, 2017.

* cited by examiner

*Primary Examiner* — Matthew Coughlin
(74) *Attorney, Agent, or Firm* — Oblon, McClelland, Maier & Neustadt, L.L.P.

(57) ABSTRACT

Imidazolone and pyrazolone derivatives of formula (I) described herein exhibit human neutrophil elastase inhibitory properties and are useful for the therapy of diseases and conditions in which HNE is implicated.

11 Claims, No Drawings

COMPOUNDS

CROSS REFERENCES TO RELATED APPLICATIONS

This application claims priority to European Patent Application No. 16172199.8, filed on May 31, 2016, which is incorporated herein by reference in its entirety.

BACKGROUND OF THE INVENTION

Field of the Invention

The present invention relates to imidazolone and pyrazolone derivatives having human neutrophil elastase inhibitory properties. The present invention also relates to the treatment of certain diseases and conditions by administering such a derivative.

Discussion of the Background

Human neutrophil elastase (HNE) is a 32 kDa serine proteinase found in the azurophilic granules of neutrophils. It has a role in the degradation of a wide range of extracellular matrix proteins, including fibronectin, laminin, proteoglycans, Type III and Type IV collagens as well as elastin (see Bieth, G. in *Regulation of Matrix accumulation*, Mecham, R. P. (Eds), Academic Press, NY, USA 1986, 217-306, which is incorporated herein by reference in its entirety). HNE has long been considered to play an important role in homeostasis through repair and disposal of damaged tissues via degradation of the tissue structural proteins. It is also relevant in the defense against bacterial invasion by means of degradation of the bacterial body. In addition to its effects on matrix tissues, HNE has been implicated in the upregulation of IL-8 gene expression and also induces IL-8 release from the epithelial cells of the lung. In animal models of Chronic Obstructive Pulmonary Disease induced by tobacco smoke exposure both small molecule inhibitors and protein inhibitors of HNE inhibit the inflammatory response and the development of emphysema (see Wright, J. L. et al. *Am. J. Respir. Crit. Care Med.* 2002, 166, 954-960; Churg, A. et al. *Am. J Respir. Crit. Care Med.* 2003, 168, 199-207, which are incorporated herein by reference in their entireties). Thus, HNE may play a role both in matrix destruction and in amplifying inflammatory responses in chronic respiratory diseases where neutrophil influx is a characteristic feature. Indeed, HNE is believed to play a role in several pulmonary diseases, including chronic obstructive pulmonary disease (COPD), cystic fibrosis (CF), acute respiratory distress syndrome (ARDS), pulmonary emphysema, pneumonia and lung fibrosis. It is also implicated in several cardiovascular diseases in which tissue remodeling is involved, for example, in heart failure and the generation of ischemic tissue injury following acute myocardial infarction.

COPD is an umbrella term encompassing three different pathological conditions, all of which contribute to limitation of airflow: chronic bronchitis, emphysema and small-airway disease. Generally all three will exist to varying extents in patients presenting with COPD, and all three may be due to neutrophil-mediated inflammation, as supported by the increased number of neutrophils observed in bronchoalveolar leakage (BAL) fluids of COPD patients (see Thompson, A. B.; Daughton, D.; et al. *Am. Rev. Respir. Dis.* 1989, 140, 1527-1537, which is incorporated herein by reference in its entirety). The major pathogenic determinant in COPD has long been considered to be the protease-anti-protease balance (also known as the "elastase:anti-elastase hypothesis"), in which an imbalance of HNE and endogenous antiproteases such as $\alpha 1$-antitrypsin ($a_1$-AT), secretory leukocyte protease inhibitor (SLPI) and pre-elafin leads to the various inflammatory disorders of COPD. Individuals that have a genetic deficiency of the protease inhibitor $\alpha 1$-antitrypsin develop emphysema that increases in severity over time (see Laurrell, C. B.; Erikkson, S *Scand. J. Clin. Invest.* 1963 15, 132-140, which is incorporated herein by reference in its entirety). An excess of HNE is therefore destructive, leading to the breakdown of pulmonary morphology with loss of elasticity and destruction of alveolar attachments of airways in the lung (emphysema) whilst simultaneously increasing microvascular permeability and mucus hypersecretion (chronic bronchitis).

Several human neutrophil inhibitors have been disclosed so far. In particular, WO 2011/110858, WO 2011/110859, WO 2014/095700, and WO 2015/091281, all of which are incorporated herein by reference in their entireties, describe pyrimidine derivatives having human neutrophil elastase inhibitory properties.

Although several HNE inhibitors have been disclosed so far as above reported, there is still a need for further HNE inhibitors. Particularly, there is still a need for further HNE inhibitors endowed with a high potency for HNE enzyme inhibition. Particularly advantageous would also be the identification of further HNE inhibitors endowed with a high potency for HNE enzyme inhibition and which would show an appropriate developability profile as an inhalation treatment.

Thus, there remains a need for improved HNE inhibitors.

SUMMARY OF THE INVENTION

Accordingly, it is one object of the present invention to provide novel imidazolone and pyrazolone derivatives having human neutrophil elastase inhibitory properties.

It is another object of the present invention to provide novel methods for the treatment of certain diseases and conditions by administering such a derivative.

These and other objects, which will become apparent during the following detailed description, have been achieved by the inventors' discovery of the compounds of formula (I) described below.

DETAILED DESCRIPTION OF THE PREFERRED EMBODIMENTS

In one aspect, the present invention provides a compound of formula (I), or a pharmaceutically acceptable salt thereof:

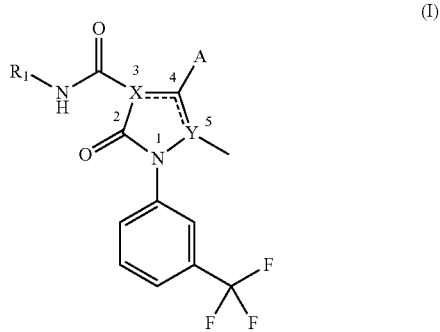

wherein
X is —C or —N;
Y is C or N, wherein X and Y are not simultaneously C or N;
$R_1$ is selected from the group consisting of linear or branched —$(C_1$-$C_6)$alkyl, —$(C_3$-$C_6)$cycloalkyl, —$(C_3$-$C_6)$heterocycloalkyl and aryl$(C_1$-$C_6)$alkylene-, wherein any of such —$(C_3$-$C_6)$cycloalkyl, —$(C_3$-$C_6)$heterocycloalkyl and aryl$(C_1$-$C_6)$alkylene- may be optionally substituted by linear or branched —$(C_1$-$C_6)$haloalkyl-C(O)—, —$(C_1$-$C_6)$alkylsulfonyl and aryl$(C_1$-$C_6)$alkylene-OC(O)—;
A is selected from

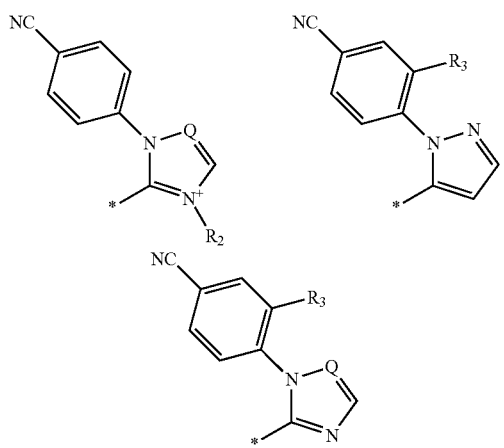

wherein
Q is —CH or N;
$R_2$ is selected from a group consisting of —$(C_1$-$C_6)$alkyl, aryl$(C_1$-$C_6)$alkylene- and heteroaryl$(C_1$-$C_6)$alkylene-;
$R_3$ is —$(C_1$-$C_6)$alkyleneN$^+R_aR_bR_c$ or heteroaryl$(C_1$-$C_6)$alkylene;
$R_a$ is —$(C_1$-$C_6)$alkyl;
$R_b$ is —$(C_1$-$C_6)$alkyl;
$R_c$ is selected from a group consisting of —$(C_1$-$C_6)$alkyl, aryl-$(C_1$-$C_6)$alkylene and heteroaryl$(C_1$-$C_6)$alkylene- or $R_a$ and $R_b$ may form an heterocycloalkyl with the N$^+$ atom, wherein such heterocycloalkyl and heteroaryl may be optionally substituted by one or more $(C_1$-$C_6)$ alkyl;
wherein the nitrogen atom in the heterocycloalkyl and heteroaryl groups may be quaternized; and
wherein the dotted lines connecting X to the carbon atom in position 4 and Y, indicate that when X is N, then the double bond is in 4-5 position, and when Y is N, then the double bond is in 3-4 position.
The compounds of formula (I) can be prepared in the form of salts, particularly pharmaceutically acceptable salts, N-oxides, hydrates, solvates and polymorphs thereof. Any reference to a compound herein, or reference to "compounds of the invention", "compounds of formula (I)", and the like includes such compounds whether or not in salt, N-oxide, hydrate, solvate or polymorphic form.
The compounds of the present invention can be used in the treatment or prevention of diseases in which HNE is implicated, for example chronic obstructive pulmonary disease (COPD), bronchiectasis, chronic bronchitis, lung fibrosis, pneumonia, acute respiratory distress syndrome (ARDS), pulmonary emphysema, smoking-induced emphysema and cystic fibrosis.

Hence other aspects of the invention are (i) a pharmaceutical composition comprising a compound of the invention and a pharmaceutically acceptable carrier or excipient; and (ii) the use of a compound of the invention for use in the treatment or prevention of a disease or condition in which HNE is implicated.

Terminology

The term "$(C_a$-$C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.
The term "$(C_a$-$C_b)$ cycloalkyl", wherein a and b are integers, refers to saturated monocyclic, bicyclic or tricyclic hydrocarbon groups containing from a to b ring carbon atoms, as appropriate. Examples include cyclopropyl, cyclobutyl, cyclopentyl, cyclohexyl and cycloheptyl, and adamantyl.
The term "heterocyclic" relates to a saturated mono-, bi- or tri-cyclic non-aromatic radical containing one or more heteroatoms selected from S, N and O. In the case of bicyclic heterocyclic systems, included within the scope of the term are fused, spiro and bridged bicyclic systems, such as for example a quinuclidine ring. In particular, the term "$C_a$-$C_b$heterocycloalkyl" refers to monocyclic $(C_a$-$C_b)$cycloalkyl groups, in which at least one ring carbon atom is replaced by a heteroatom (e.g. N, NH, S or O). Examples of $(C_a$-$C_b)$ heterocycloalkyl include pyrrolidinyl, thiazolidinyl, piperazinyl, piperidinyl, morpholinyl, and thiomorpholinyl.
By analogy, the expression "heterocycloalkylenee" refers to a divalent heterocyclic radical as above defined. In particular, the expression "$(C_a$-$C_b)$heterocycloalkylenee" refers to a divalent $(C_a$-$C_b)$heterocycloalkyl radical (such as for example pyrrolidinene) wherein "$(C_a$-$C_b)$heterocycloalkyl group is as above defined.
The expression "heteroaryl" refers to mono or bi-cyclic ring systems with 5 to 11 ring atoms, in which at least one ring is aromatic and in which at least one ring atom is a heteroatom (e.g. N, NH, S or O).
Examples of suitable 5,6-membered heteroaryl monocyclic systems include, for instance thiophene (thiophenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), pyrimidine (pyrimidinyl), pyridazine (pyridazinyl), and furan (furanyl) radicals and the like.
Examples of suitable bi-cyclic heteroaryl ring systems include quinolones (quinolonyl), isoquinolines (isoquinolinyl), indole (indolyl), isoindole (isoindolyl), indolizine (indolizinyl), benzimidazole (benzimidazolyl), azabenzimidazole (azabenzimidazolyl), benzoxazole (benzoxazolyl), and benzothiazole (benzthiazolyl) radicals and the like.
The expression "$(C_a$-$C_b)$alkylsulfonyl" refers to —SO$_2$$(C_a$-$C_b)$alkyl groups wherein the group "$(C_a$-$C_b)$alkyl" has the meaning above defined.
The term "pharmaceutically acceptable salts" refers to derivatives of compounds of formula (I) wherein the parent compound is modified by converting any of the free acid or basic group, if present, into the corresponding addition salt with any base or acid conventionally intended as being pharmaceutically acceptable.
Where the compounds of the present invention have at least one stereogenic center, they can exist as enantiomers. When the compounds according to the invention possess two or more stereogenic centers, they can additionally exist as diastereoisomers. It is to be understood that all such isomers and mixtures thereof in any proportion are encompassed within the scope of the present invention.

It is to be understood that all preferred groups or embodiments described here below for compounds of formula (I) may be combined among each other mutatis mutandis.

In one embodiment for compounds of formula (I) X is C or N.

In another embodiment, Y is C or N, wherein X and Y are not simultaneously C or N.

In another embodiment, X is C and Y is N.

In another embodiment, X is N and Y is C.

In another embodiment, A is

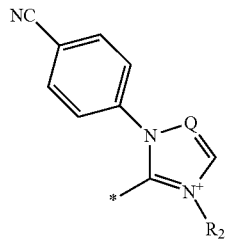

wherein Q is CH or N, $R_2$ is selected from a group consisting of —($C_1$-$C_6$)alkyl and aryl($C_1$-$C_6$)alkylene-.

In another embodiment, A is

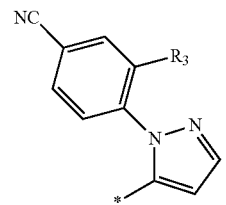

wherein $R_3$ is —($C_1$-$C_6$)alkyleneN$^+$$R_a$$R_b$$R_c$, wherein $R_a$ and $R_b$ are independently —($C_1$-$C_6$)alkyl; $R_c$ is selected from a group consisting of —($C_1$-$C_6$)alkyl, aryl-($C_1$-$C_6$)alkylene- and heteroaryl($C_1$-$C_6$)alkylene-.

In another embodiment, a compound of the invention is selected in the group consisting of

| Example | Chemical name |
|---|---|
| 1 | 1-(4-Cyanophenyl)-2-{3-(cyclopentylcarbamoyl)-5-methyl-2-oxo-1-[3-(trifluoromethyl)phenyl]-2,3-dihydro-1H-imidazol-4-yl}-3-methyl-1H-imidazol-3-ium benzene sulfonate |
| 2 | 1-(4-Cyanophenyl)-2-{3-(cyclopentylcarbamoyl)-5-methyl-2-oxo-1-[3-(trifluoromethyl)phenyl]-2,3-dihydro-1H-imidazol-4-yl}-3-benzyl-1H-imidazol-3-ium bromide |
| 3 | 1-(4-Cyanophenyl)-2-{3-(cyclobutylcarbamoyl)-5-methyl-2-oxo-1-[3-(trifluoromethyl)phenyl]-2,3-dihydro-1H-imidazol-4-yl}-3-methyl-1H-imidazol-3-ium benzene sulfonate |
| 4 | 1-(4-Cyanophenyl)-2-{3-[1-(2,2,2-trifluoro-acetyl)-piperidin-4-ylcarbamoyl]-5-methyl-2-oxo-1-[3-(trifluoromethyl)phenyl]}-2,3-dihydro-1H-imidazol-4-yl}-3-methyl-1H-imidazol-3-ium benzene sulfonate |
| 5 | 1-(4-Cyanophenyl)-2-{3-(4-methanesulfonyl-benzylcarbamoyl)-5-methyl-2-oxo-1-[3-(trifluoromethyl)phenyl]-2,3-dihydro-1H-imidazol-4-yl}-3-methyl-1H-imidazol-3-ium benzene sulfonate |
| 6 | 1-(4-Cyano-phenyl)-5-[3-cyclopentylcarbamoyl-5-methyl-2-oxo-1-(3-trifluoromethyl-phenyl)-2,3-dihydro-1H-imidazol-4-yl]-4-methyl-1H-[1,2,4]triazol-4-ium benzene sulfonate |
| 7 | 3-(4-Cyano-phenyl)-2-[4-cyclopentylcarbamoyl-2-methyl-5-oxo-1-(3-trifluoromethyl-phenyl)-2,5-dihydro-1H-pyrazol-3-yl]-1-methyl-3H-imidazol-1-ium benzenesulfonate |
| 8 | 1-(4-cyano-phenyl)-5-[4-cyclopentylcarbamoyl-2-methyl-5-oxo-1-(3-trifluoromethyl-phenyl)-2,5-dihydro-1H-pyrazol-3-yl]-4-methyl-1H-[1,2,4]triazol-4-ium benzenesulfonate |
| 9 | [2-(5-Cyano-2-{5-[3-cyclopentylcarbamoyl-5-methyl-2-oxo-1-(3-trifluoromethyl-phenyl)-2,3-dihydro-1H-imidazol-4-yl]-pyrazol-1-yl}-phenyl)-ethyl]-trimethyl-ammonium benzene sulfonate |
| 10 | Benzyl-[2-(5-cyano-2-{5-[3-cyclopentylcarbamoyl-5-methyl-2-oxo-1-(3-trifluoromethyl-phenyl)-2,3-dihydro-1H-imidazol-4-yl]-pyrazol-1-yl}-phenyl)-ethyl]-dimethyl-ammonium bromide |
| 11 | [2-(5-Cyano-2-{5-[3-cyclohexylcarbamoyl-5-methyl-2-oxo-1-(3-trifluoromethyl-phenyl)-2,3-dihydro-1H-imidazol-4-yl]-pyrazol-1-yl}-phenyl)-ethyl]-trimethyl-ammonium benzene sulphonate |
| 12 | [2-(5-Cyano-2-{5-[3-cyclopropylcarbamoyl-5-methyl-2-oxo-1-(3-trifluoromethyl-phenyl)-2,3-dihydro-1H-imidazol-4-yl]-pyrazol-1-yl}-phenyl)-ethyl]-trimethyl-ammonium benzene sulphonate |
| 13 | [2-(5-Cyano-2-{5-[3-ethylcarbamoyl-5-methyl-2-oxo-1-(3-trifluoromethyl-phenyl)-2,3-dihydro-1H-imidazol-4-yl]-pyrazol-1-yl}-phenyl)-ethyl]-trimethyl-ammonium benzene sulphonate |
| 14 | [2-(5-Cyano-2-{5-[3-isopropylcarbamoyl-5-methyl-2-oxo-1-(3-trifluoromethyl-phenyl)-2,3-dihydro-1H-imidazol-4-yl]-pyrazol-1-yl}-phenyl)-ethyl]-trimethyl-ammonium benzene sulphonate |
| 15 | (2-{5-Cyano-2-[4'-cyclopentylcarbamoyl-2'-methyl-5'-oxo-1'-(3-trifluoromethyl-phenyl)-2',5'-dihydro-1'H-[3,3']bipyrazolyl-2-yl]-phenyl}-ethyl)-trimethyl-ammonium benzene sulfonate |
| 16 | Benzyl-(2-{5-cyano-2-[4'-cyclopentylcarbamoyl-2'-methyl-5'-oxo-1'-(3-trifluoromethyl-phenyl)-2',5'-dihydro-1'H-[3,3']bipyrazolyl-2-yl]-phenyl}-ethyl)-dimethyl-ammonium bromide |
| 17 | (2-{5-Cyano-2-[4'-cyclohexylcarbamoyl-2'-methyl-5'-oxo-1'-(3-trifluoromethyl-phenyl)-2',5'-dihydro-1'H-[3,3']bipyrazolyl-2-yl]-phenyl}-ethyl)-trimethyl-ammonium benzene sulfonate |

The therapeutic utility of the present compounds is pertinent to any disease that is known to be at least partially mediated by the action of human neutrophil elastase. For example, the present compounds can be beneficial in the treatment of chronic obstructive pulmonary disease (COPD), cystic fibrosis (CF), bronchiectasis, acute respiratory distress syndrome (ARDS), pulmonary emphysema, pneumonia and lung fibrosis.

Compounds of the invention are useful for treatment of inflammatory respiratory disorders, for example asthma (mild, moderate or severe), steroid resistant asthma, bronchitis, chronic obstructive pulmonary disease (COPD), cystic fibrosis (CF), pulmonary edema, pulmonary embolism, pneumonia, pulmonary sarcoidosis, pulmonary emphysema, silicosis, pulmonary fibrosis, pulmonary hypertension, respiratory failure, acute respiratory distress syndrome (ARDS), emphysema, chronic bronchitis, tuberculosis, aspergillosis and other fungal infections, hypersensitivity pneumonitis, vasculitic and thrombotic disorders of the lung vasculature, antitussive activity including treatment of chronic cough associated with inflammatory and secretory conditions of the airways, infection due to respiratory syncytial virus, influenza, coronavirus (including severe acute respiratory syndrome, SARS) and adenovirus, bronchiectasis and lung cancer.

The present invention is also concerned with pharmaceutical formulations comprising, as an active ingredient, a compound of the invention. Other compounds can be combined with compounds of this invention for the prevention and treatment of inflammatory diseases of the lung. Thus the present invention is also concerned with pharmaceutical compositions for preventing and treating inflammatory diseases of the lung comprising a therapeutically effective amount of a compound of the invention and one or more other therapeutic agents.

Suitable therapeutic agents for a combination therapy with compounds of the invention include: (1) a corticosteroid, for example budesonide, beclomethasone, beclomethasone (e.g., as the mono or the dipropionate ester), flunisolide, fluticasone (e.g. as the propionate or furoate ester), Ciclesonide, mometasone (e.g. as the furoate ester), mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocortisone, desoxycorticosterone, rofleponide, etiprednol dicloacetate and the like.

Steroid drugs can additionally include steroids in clinical or pre-clinical development for respiratory diseases such as GW-685698, GW-799943, GSK 870086, QAE397, NCX-1010, NCX-1020, NO-dexamethasone, PL-2146, NS-126 (formerly ST-126). Steroid drugs can also additionally include next generation molecules in development with reduced side effect profiles such as selective glucocorticoid receptor agonists (SEGRAs), including ZK-216348 and AZD5423; (2) a P32-adrenoreceptor agonist, such as albuterol, bambuterol, terbutaline, fenoterol, formoterol, formoterol fumarate, salmeterol, salmeterol xinafoate, arformoterol, arfomoterol tartrate, indacaterol (QAB-149), carmoterol, BI 1744 CL, GSK159797 (milveterol), GSK59790, GSK159802, GSK642444 (vilanterol), GSK678007, GSK96108, clenbuterol, procaterol, bitolterol, LAS 100977 (abediterol), BI1744CL (olodaterol) and brodxaterol; (3) a leukotriene modulator, for example montelukast, zafirlukast or pranlukast; (4) anticholinergic agents, for example selective muscarinic-3 (M3) receptor antagonists such as ipratropium bromide, tiotropium, tiotropium bromide (Spiriva®), glycopyrronium bromide, aclidinium bromide, LAS34273, GSK656398, GSK233705, GSK 573719 (umeclidinium), LAS35201, QAT370 and oxytropium bromide; (5) phosphodiesterase-IV (PDE-IV) inhibitors, for example roflumilast, cilomilast or theophylline; (6) an antitussive agent, such as codeine or dextramorphan; and (7) a non-steroidal anti-inflammatory agent (NSAID), for example ibuprofen or ketoprofen; (8) a mucolytic, for example N acetyl cysteine or fudostein; (9) an expectorant/mucokinetic modulator, for example ambroxol, hypertonic solutions (e.g. saline or mannitol) or surfactant; (10) a peptide mucolytic, for example recombinant human deoxyribonuclease I (dornase-alfa and rhDNase) or helicidin; (11) antibiotics, for example azithromycin, tobramycin and aztreonam; and (12) p38 Mitogen Activated Protein (MAP) kinase inhibitors, such as GSK 856553 and GSK 681323; (12) inhibitors of Janus Kinases (JAK) such as CP-690550 or GLPG0634; (13) Spleen Tyrosine Kinase (SYK) inhibitors such as R406, R343 or PRT062607; (14) inhibitors of delta and/or gamma isoforms of Phosphatidylinositol 3-kinase (PI3K).; (15) anti-retroviral agents such as ribavirin, zanamivir or laninamivir; (16) PPAR-γ agonists such as pioglitazone and rosiglitazone.

In one aspect, the present invention concerns the use of inhaled administration of compounds of the invention in combination with other anti-inflammatory drugs and bronchodilator drug combinations (i. e. triple combination product), including but not limited to salmeterol xinafoate/fluticasone propionate (Advair/Seretide®), vilanterol/fluticasone furoate (BREO ELLIPTA™), formoterol fumarate/budesonide (Symbicort®), formoterol fumarate/mometasone furoate, formoterol fumarate/beclometasone dipropionate (Foster®), formoterol fumarate/fluticasone propionate (FlutiForm®), Indacaterol/mometasone furoate, Indacaterol/QAE-397, GSK159797/GSK 685698, GSK159802/GSK 685698, GSK642444/GSK 685698, formoterol fumarate/ciclesonide, arformoterol tartrate/ciclesonide.

In another aspect, the invention concerns the use of inhaled administration of compounds of the invention in combination with other bronchodilator drug combinations, particularly β$_2$ agonist/M$_3$ antagonist combinations (i.e. triple combination product), including but not limited to salmeterol xinafoate/tiotropium bromide, formoterol fumarate/tiotropium bromide, formoterol fumarate/glycopyrrolate (PT003), BI 1744 CL/tiotropium bromide, indacaterol/NVA237, indacterol/QAT-370, formoterol/LAS34273, umeclidinium/vilanterol (Anoro™), GSK159797/GSK 573719, GSK159802/GSK 573719, GSK642444/GSK 573719, GSK159797/GSK 233705, GSK159802/GSK 233705, GSK642444/GSK 233705.

The weight ratio of the first and second active ingredients can be varied and will depend upon the effective dose of each ingredient. Generally, an effective dose of each will be used.

The magnitude of prophylactic or therapeutic dose of a compound of the invention will, of course, vary with the nature of the severity of the condition to be treated and with the particular compound and its route of administration, and will generally be determined by clinical trial as required in the pharmaceutical art. It will also vary according to the age, weight and response of the individual patient. In general, the daily dose range will lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it can be necessary to use dosages outside these limits in some cases.

Another aspect of the present invention concerns pharmaceutical compositions which comprise a compound of the invention and a pharmaceutically acceptable carrier. The pharmaceutical compositions of the invention comprise a compound of the invention as an active ingredient or a pharmaceutically acceptable salt thereof, and can also contain a pharmaceutically acceptable carrier and optionally other therapeutic ingredients.

Any suitable route of administration can be employed for providing a mammal, especially a human, with an effective dosage of a compound of the invention. In therapeutic use, the active compound can be administered by any convenient, suitable or effective route. Suitable routes of administration are known, and include oral, intravenous, rectal, parenteral, topical, ocular, nasal, buccal and pulmonary (by inhalation).

Compositions suitable for administration by inhalation are known, and can include carriers and/or diluents that are known for use in such compositions. The composition can contain 0.01-99% by weight of active compound. Preferably, a unit dose comprises the active compound in an amount of 1 µg to 10 mg.

The most suitable dosage level can be determined by any known suitable method. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease to be treated.

For delivery by inhalation, the active compound is preferably in the form of microparticles. They can be prepared by a variety of techniques, including spray-drying, freeze-drying and micronization.

By way of example, a composition of the invention can be prepared as a suspension for delivery from a nebuliser or as an aerosol in a liquid propellant, for example for use in a pressurised metered dose inhaler (PMDI). Propellants suitable for use in a PMDI are known and include CFC-12, HFA-134a, HFA-227, HCFC-22 (CCl2F2) and HFA-152 (CH4F2 and isobutane).

In a preferred embodiment, a composition is in dry powder form, for delivery using a dry powder inhaler (DPI). Many types of DPI are known.

Microparticles for delivery by administration can be formulated with excipients that aid delivery and release. For example, in a dry powder formulation, microparticles can be formulated with large carrier particles that aid flow from the DPI into the lung. Suitable carrier particles are known, and include lactose particles; they can have a mass median aerodynamic diameter of greater than 90 µm.

In the case of an aerosol-based formulation, a preferred composition is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The compounds of the present invention can be used in combination with other drugs that are used in the treatment/prevention/suppression or amelioration of the diseases or conditions for which present compounds are useful. Such other drugs can be administered, by a route and in an amount commonly used therefore, contemporaneously or sequentially with a compound of the invention. When a compound of the present invention is used contemporaneously with one or more other drugs, a pharmaceutical composition containing such other drugs in addition to the compound of the present invention is preferred. Accordingly, the pharmaceutical compositions of the invention include those that also contain one or more other active ingredients, in addition to a compound of the invention.

The agents of the present invention can be administered in inhaled form. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compounds can be dosed as described depending on the inhaler system used. In addition to the active compounds, the administration forms can additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0 505 321, which is incorporated herein by reference in its entirety).

Procedure for the preparation of compounds of formula (I)

The present invention further provides a process for the preparation of a compound of formula (I) or a pharmaceutically acceptable salt or quaternary salt thereof as defined above. Compounds of the invention (I) may be prepared according to routes illustrated below in Schemes A, B and C.

The skilled person may introduce, where appropriate, suitable variations to the conditions specifically described in the experimental in order to adapt the synthetic routes to the provision of further compounds of the invention. Such variations may include, but are not limited to, use of appropriate starting materials to generate different compounds, changes in the solvent and temperature of reactions, replacements of reagents with analogous chemical role, introduction or removal of protection/deprotection stages of functional groups sensitive to reaction conditions and reagents.

Also, introduction or removal of specific synthetic steps oriented to further functionalization of the chemical scaffold may be contemplated and is included within the scope of the present invention. Processes which can be used and are described and reported in Examples and Schemes, should not be viewed as limiting the scope of the synthetic methods available for the preparation of the compounds of the present invention.

Compounds used as starting materials or intermediates may be commercially available, their preparation may be specifically described in the literature, or they may be prepared according to known methods. In some instances, procedures for the preparation of intermediates or starting materials may be also provided in the experimental.

The process described is particularly advantageous as it is susceptible of being properly modulated, through any proper known variant, so as to obtain any of the desired compounds of the invention. Such variants are comprised within the scope of the present invention.

From all of the above, it should be clear that any of the described groups may be present as such or in any properly protected form.

In particular, functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known (see, for a general reference, T. W. Green; Protective Groups in Organic Synthesis (Wiley, N.Y. 1981) which is incorporated herein by reference in its entirety).

Likewise, selective protection and deprotection of any of the said groups, for instance including carbonyl, hydroxyl or amino groups, may be accomplished according to very well-known methods commonly employed in organic synthetic chemistry.

From all of the above, it should be clear that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

In the following Schemes, for compounds of formula (I) to (XXI), unless otherwise indicated, groups A and $R_1$ have the same meanings as described for compounds of formula (I) above.

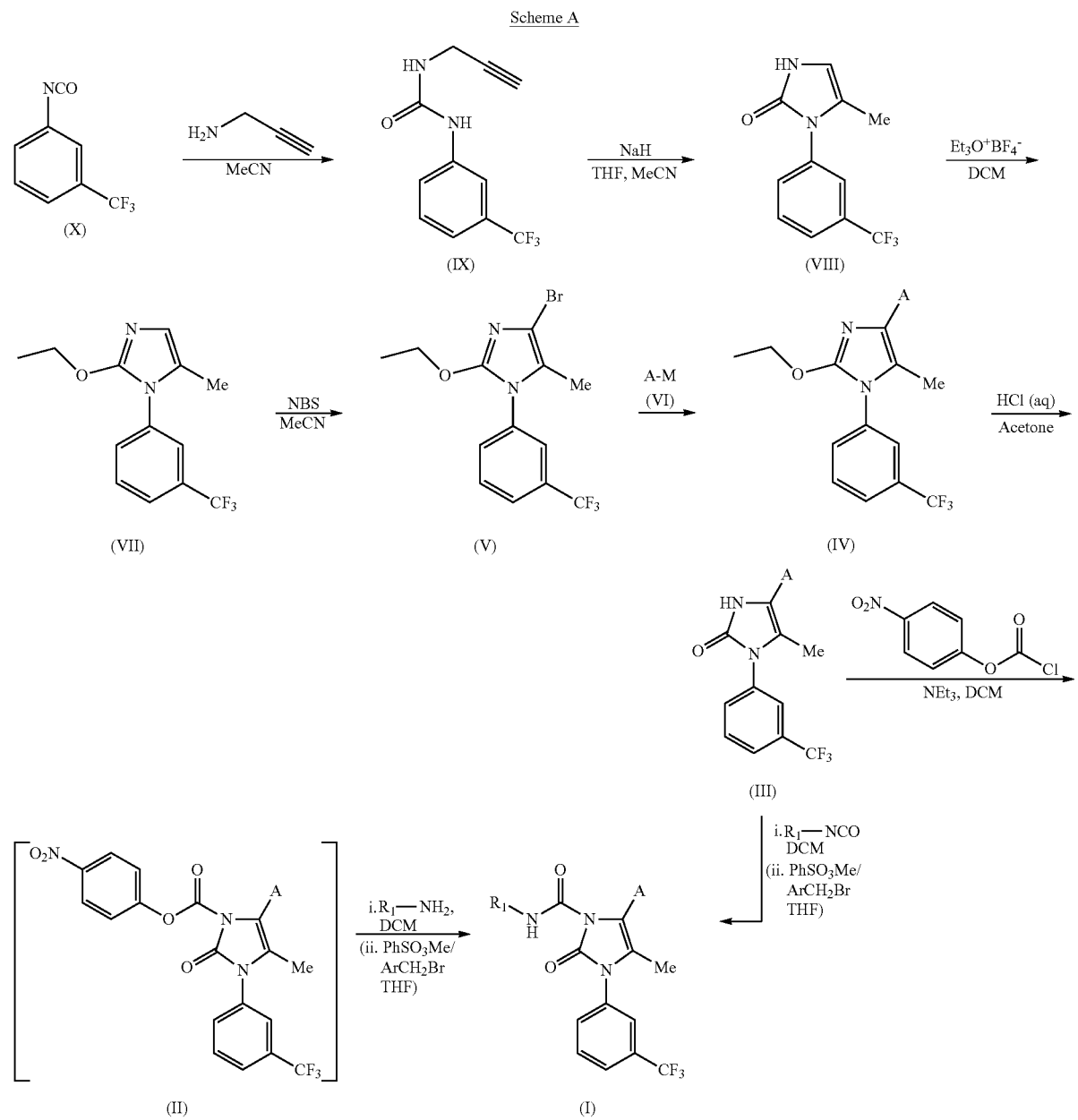

Compounds of formula (I) in Scheme A may be prepared from compounds of formula (III) by reaction with a chloroformate or equivalent such as para-nitrophenol chloroformate in the presence of a base such as triethylamine in a solvent such as dichloromethane at an appropriate temperature of between 0° C. and the boiling point of the solvent. This gives activated carbamate of formula (II) which can subsequently be reacted with an amine of formula X—$NH_2$ in a solvent such as dichloromethane at an appropriate temperature of between 0° C. and the boiling point of the solvent to give compounds of formula (I).

Compounds of formula (I) may also be prepared from compounds of formula (III) by reaction with an appropriate isocyanate of formula X—NCO or equivalent in a suitable solvent such as dichloromethane at an appropriate temperature of between 0° C. and the boiling point of the solvent.

In the instances where compounds of formula (I) contain a quaternary ammonium moiety then a quaternization step may also be used. This can be carried out by reaction with an alkylating agent such as methyl benzenesulphonate or benzyl bromide in a solvent such as THF at an appropriate temperature between ambient and the boiling point of the solvent.

A compound of formula (III) may be synthesized from a compound of formula (IV) by deprotection using an acid such as an aqueous hydrochloric acid solution in a solvent such as acetone at an appropriate temperature between 0° C. and the boiling point of the solvent.

A compound of formula (IV) may be synthesized from a compound of formula (V) by palladium coupling with a suitable partner fragment of formula (VI) wherein M may be an halide, for example, bromide. The coupling can be carried out with a suitable catalyst such as 2-dicyclohexylphosphino-2',4',6'-triisopropylbiphenyl, (2-dicyclohexylphosphino-2',4',6'-triisopropyl-1,1'-biphenyl)palladium(II) dichloride and tetrahydroxydiboron in the presence of potassium acetate and $K_2CO_3$ in an appropriate solvent such as ethanol at a suitable temperature between ambient and the boiling point of the solvent.

A compound of formula (V) may be synthesized from a compound of formula (VII) by bromination using a reagent such as N-bromosuccinimide in an appropriate solvent such as acetonitrile at a suitable temperature between 0° C. and the boiling point of the solvent.

A compound of formula (VII) may be synthesized from a compound of formula (VIII) by ethylation using a regent such as Meerwein's reagent ($Et_3O^+BF_4^-$) in an appropriate solvent such as dichloromethane at a suitable temperature between 0° C. and the boiling point of the solvent.

A compound of formula (VIII) may be synthesized from a compound of formula (IX) using a strong base such as sodium hydride in an appropriate solvent such as tetrahydrofuran/acetonitrile at a suitable temperature between 0° C. and the boiling point of the solvent.

A compound of formula (IX) maybe synthesized from a compound of formula (X) by reaction with an amine such as propargylamine in an appropriate solvent such as acetonitrile at a suitable temperature between 0° C. and the boiling point of the solvent.

An alternative route to some compounds of formula (III) is outlined in Scheme B.

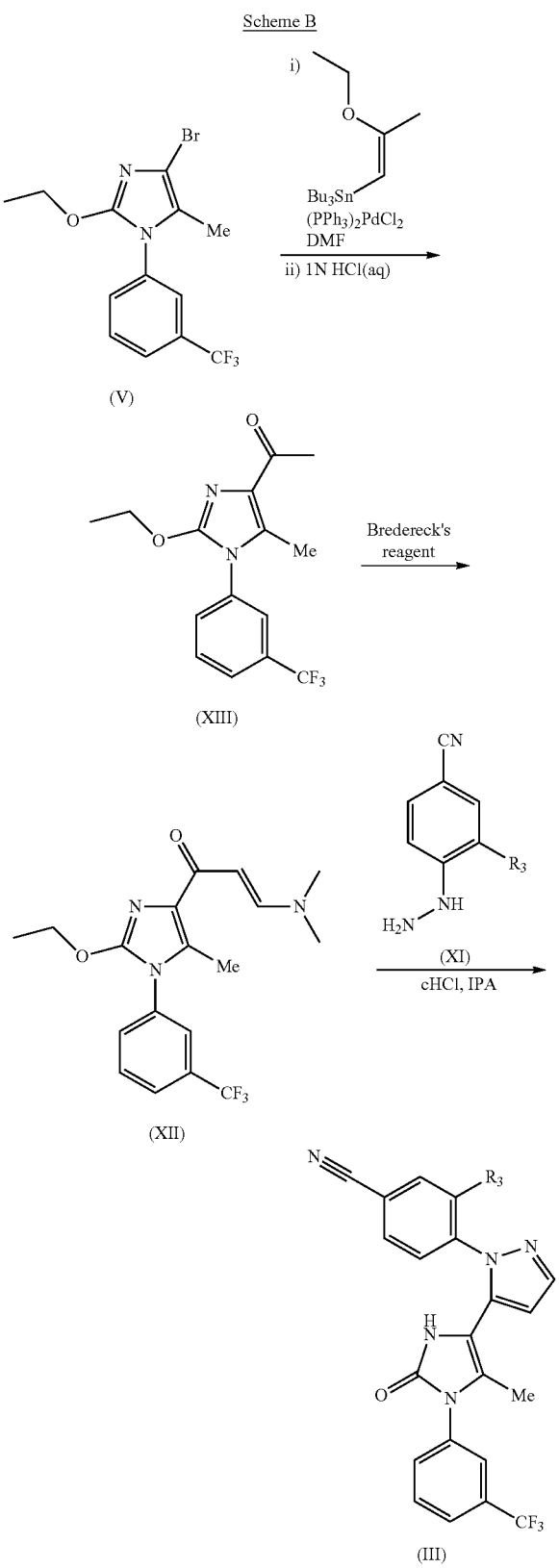

Scheme B

Compounds of formula (III) in Scheme B may be prepared from a compound of formula (XII) by reaction with a compound of formula (XI) in the presence of an acid such as concentrated hydrochloric in an appropriate solvent such as IPA at a suitable temperature between 0° C. and the boiling point of the solvent.

A compound of formula (XII) may be prepared from a compound of formula (XIII) by using a suitable reagent such as Bredereck's reagent at an appropriate temperature between 0° C. and the boiling point of the mixture.

A compound of formula (XIII) may be prepared from a compound of formula (V) by reaction with a reagent such as tributyl(1-ethoxyvinyl)tin in the presence of a suitable catalyst such as bis(triphenylphosphine)palladium(II) dichloride in an appropriate solvent such as DMF at a temperature between 0° C. and the boiling point of the solvent. The intermediate enol ether can then be hydrolysed with a suitable acid such as 1N aqueous hydrochloric acid to give ketone (XIII).

An alternative route to a subset of compounds of formula (I) is outlined in Scheme C.

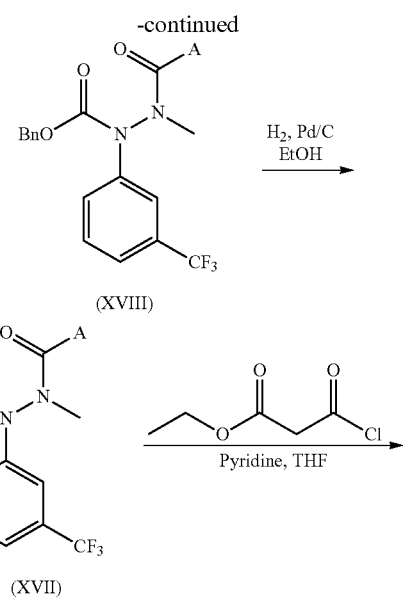

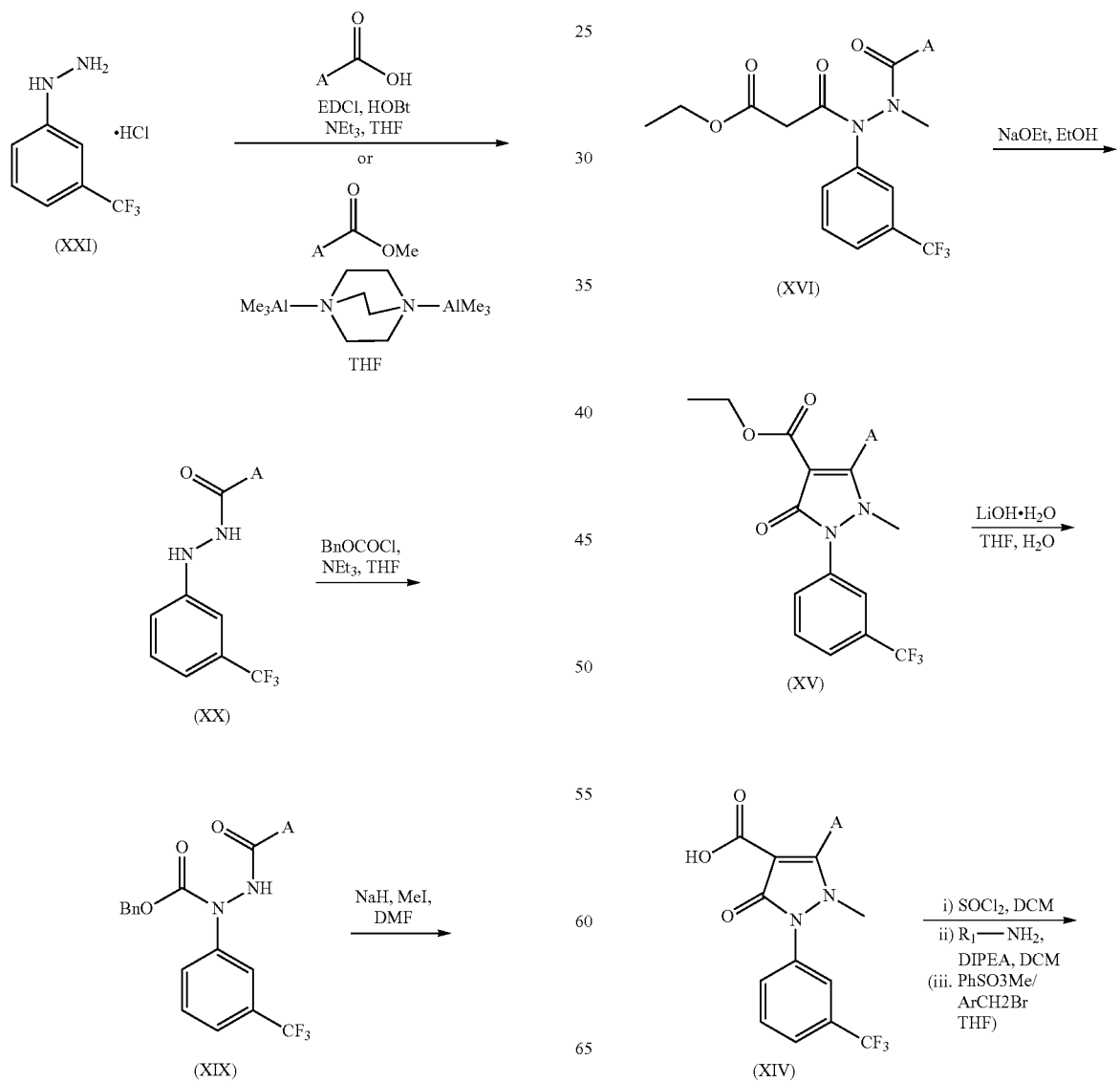

-continued

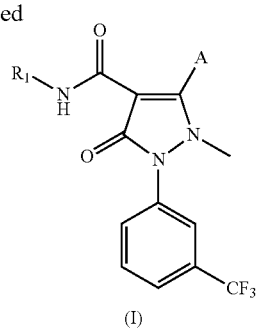

(I)

Compounds of formula (I) in Scheme C may be prepared from a compound of formula (XIV) by amide coupling with an amine of formula $R_1$—$NH_2$. This may be done using an appropriate coupling reagent such as CDI in a suitable solvent such as THF at an appropriate temperature between 0° C. and the boiling point of the mixture. Alternatively a reagent such as thionyl chloride in a solvent such as DCM could be used to form an intermediate acid chloride which can then react with the amine of formula $R_1$—$NH_2$ in an appropriate solvent like DCM in the presence of a suitable base such as DIPEA at a temperature between 0° C. and the boiling point of the mixture.

In the instances where compounds of formula (I) contain a quaternary ammonium moiety then a quaternization step may also be used. This can be carried out by reaction with an alkylating agent such as methyl benzenesulphonate or benzyl bromide in a solvent such as THF at an appropriate temperature between ambient and the boiling point of the solvent.

Compounds of formula (XIV) may be synthesized from compounds of formula (XV) by hydrolysis using suitable conditions such as lithium hydroxide in a mixture of water and THF at an appropriate temperature between 0° C. and the boiling point of the mixture.

Compounds of formula (XV) may be prepared from compounds of formula (XVI) by reaction with a suitable base such as sodium ethoxide in an appropriate solvent such as ethanol at a temperature between 0° C. and the boiling point of the mixture.

Compounds of formula (XVI) may be prepared from compounds of formula (XVII) by reaction with ethyl malonyl chloride in the presence of a suitable base such as pyridine in a solvent such as THF at an appropriate temperature between 0° C. and the boiling point of the solvent.

Compounds of formula (XVII) may be synthesized from compounds of formula (XVIII) by deprotection using a technique such as hydrogenolysis for example with hydrogen gas in the presence of a catalyst such as palladium on activated carbon in a suitable solvent such as ethanol at an appropriate temperature between 0° C. and the boiling point of the solvent.

Compounds of formula (XVIII) may be synthesized from compounds of formula (XIX) by reaction with a methylating reagent such as methyl iodide in the presence of a base such as sodium hydride in an appropriate solvent such as DMF at a suitable temperature between 0° C. and the boiling point of the solvent.

Compounds of formula (XIX) may be prepared from compounds of formula (XX) by using a suitable protection reagent such as benzyl chloroformate in the presence of a base such as triethylamine in an appropriate solvent such as THF at a suitable temperature between 0° C. and the boiling point of the solvent.

Compounds of formula (XX) may be prepared from a compound of formula (XXI) by coupling with a compound of formula A-$CO_2$H using reagents such as EDCI and HOBt in the presence of a base such as triethylamine in a suitable solvent such as THF at an appropriate temperature between 0° C. and the boiling point of the solvent. An alternative may be condensation of a compound of formula (XXI) with a compound of formula A-$CO_2$Me using a reagent such as bis(trimethylaluminum)-1,4-diazabicyclo[2.2.2]-octane in a suitable solvent such as THF at an appropriate temperature between 0° C. and the boiling point of the solvent.

Other features of the invention will become apparent in the course of the following descriptions of exemplary embodiments which are given for illustration of the invention and are not intended to be limiting thereof.

EXAMPLES

Reactions were not carried out under an inert atmosphere unless specified and all solvents and commercial reagents were used as received.

Purification by chromatography refers to purification using the CombiFlash® Companion purification system or the Biotage SPI purification system. Where products were purified using an Isolute® SPE Si II cartridge, 'Isolute SPE Si cartridge' refers to a pre-packed polypropylenee column containing unbonded activated silica with irregular particles with average size of 50 m and nominal 60 Å porosity. Fractions containing the required product (identified by TLC and/or LCMS analysis) were pooled and concentrated in vacuo. Where HPLC was used for purification (Purification by MDAP) fractions containing the required product (identified by TLC and/or LCMS analysis) were pooled, the bulk of the organic fraction removed by evaporation, and the remaining aqueous fraction lyophilized, to give the final product. Alternatively the pooled product fraction was evaporated to dryness under reduced pressure. Where thin layer chromatography (TLC) has been used, it refers to silica gel TLC using plates, typically 3×6 cm silica gel on aluminum foil plates with a fluorescent indicator (254 nm), (e.g. Fluka 60778). Microwave experiments were carried out using a Biotage Initiator 60™ which uses a single-mode resonator and dynamic field tuning. Temperature from 40-250° C. can be achieved, and pressures of up to 30 bar can be reached.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane.

Compound names were generated using ACD/Name 2012 or AutoNom.

Analytical LC-MS Conditions

LC-MS Method 1

The Waters ZQ quadrupole mass spectrometer with a C18-reverse-phase column (30×4.6 mm Phenomenex Luna 3 μm particle size), elution with A: water+0.1% formic acid; B: MeCN+0.1% formic acid. Gradient:

| Gradient - Time | flow (mL/min) | % A | % B |
| --- | --- | --- | --- |
| 0.00 | 2.0 | 95 | 5 |
| 0.30 | 2.0 | 95 | 5 |
| 4.30 | 2.0 | 5 | 95 |

-continued

| Gradient - Time | flow (mL/min) | % A | % B |
|---|---|---|---|
| 5.30 | 2.0 | 5 | 95 |
| 5.80 | 2.0 | 95 | 5 |
| 6.00 | 2.0 | 95 | 5 |

Detection - MS, UV (200 μl/min split to the ESI source with in-line HP1100 PDA detector)
MS ionization method - Electrospray (positive and negative ion)

LC-MS Method 2

Waters Micromass ZMD quadrupole mass spectrometer with a C18-reverse-phase column (30×4.6 mm Phenomenex Luna 3 m particle size), elution with A: water+0.1% formic acid; B: MeCN+0.1% formic acid. Gradient:

| Gradient - Time | flow (mL/min) | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection - MS, ELS, UV (200 μl split to MS with in-line UV detector)
MS ionization method - Electrospray (positive and negative ion)

LC-MS Method 3

Waters Micromass ZQ2000 mass spectrometer with a C18-reverse-phase column (100×2.1 mm Acquity BEH with 1.7 m particle size) maintained at 40° C., elution with A: water+0.1% formic acid; B: MeCN+0.1% formic acid. Alternatively, where specified, a C18-reverse-phase (100× 2.1 mm Acquity UPLC BEH Shield 1.7 m particle size) column was used.
Gradient:

| Gradient - Time | flow (mL/min) | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection - MS, UV PDA
MS ionization method - Electrospray (positive and negative ion).

LC-MS Method U2

Acquity H-Class (quaternary pump/PDA detector) plus QDa Mass Spectrometer with an Acquity UPLC BEH C18-reverse-phase column (1.7 m particle size, 50×2.1 mm at 40° C.), elution with A: water+0.1% formic acid; B: MeCN+ 0.1% formic acid.
Gradient:

| Gradient - Time | flow (mL/min) | % A | % B |
|---|---|---|---|
| 0.00 | 1.0 | 97 | 3 |
| 1.50 | 1.0 | 1 | 99 |
| 1.90 | 1.0 | 1 | 99 |
| 2.00 | 1.0 | 97 | 3 |
| 2.50 | 1.0 | 97 | 3 |

Detection - MS, UV
MS ionization method - Electrospray (positive and negative ion).

Abbreviations Used in the Experimental Section:

| | |
|---|---|
| DCM | Dichloromethane |
| DIPEA | Di-isopropylethylamine |
| DMF | N,N-dimethylformamide |
| DMSO | Dimethylsulphoxide |
| Et$_2$O | Diethyl ether |
| EtOAc | Ethyl acetate |
| h | Hour |
| HPLC | High performance liquid chromatography |
| IMS | Industrial methylated spirits |
| LC-MS | Liquid chromatography-mass spectrometry |
| MeCN | Acetonitrile |
| Min | Minutes |
| NBS | N-Bromosuccinimide |
| Rt | Retention time |
| RT | Room temperature |
| THF | Tetrahydrofuran |

In the procedures that follow, some of the starting materials are identified through an "Intermediate" or "Example" number. The starting material may not necessarily have been prepared from the batch referred to.

When reference is made to the use of a "similar" or "analogous" procedure, such a procedure may involve minor variations, for example reaction temperature, reagent/solvent amount, reaction time, work-up conditions or chromatographic purification conditions.

Example 1. 1-(4-Cyanophenyl)-2-{3-(cyclopentyl-carbamoyl)-5-methyl-2-oxo-1-[3-(trifluoromethyl) phenyl]-2,3-dihydro-1H-imidazol-4-yl}-3-methyl-1H-imidazol-3-ium benzene sulfonate

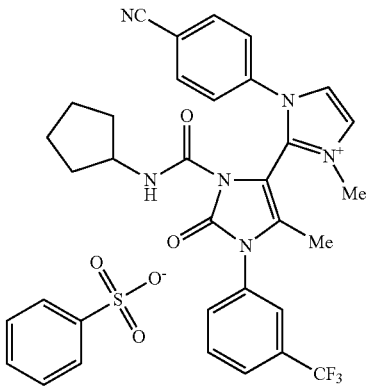 [SMILES: O=S(=O)([O-])c1ccccc1 ; Cc1c(-c2n(-c3ccc(C#N)cc3)cc[n+]2C)n(C(=O)NC2CCCC2)c(=O)n1-c1cccc(C(F)(F)F)c1]

Intermediate 1A.
1-(prop-2-ynyl)-3-[3-(trifluoromethyl)phenyl]urea

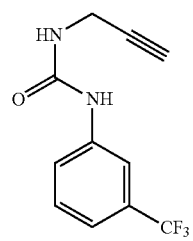 [SMILES: C#CCNC(=O)Nc1cccc(C(F)(F)F)c1]

A solution of propargyl amine (4.41 g, 5.13 mL, 80 mmol) in MeCN (30 mL) was added to a stirred solution of 3-(trifluoromethyl)phenyl isocyanate (15.0 g, 12.12 mL, 80 mmol) in MeCN (60 mL) under a nitrogen atmosphere. The reaction mixture was cooled with a RT cooling bath and the rate of addition was such that the internal temperature did not exceed 35° C. After 1.5 h the mixture was concentrated in vacuo. EtOAc (10 ml) was added to the residue and the mixture was sonicated for 2 minutes. The resultant slurry was diluted with cyclohexane (40 ml). The mixture was stirred for 10 minutes and the solid was then recovered by filtration. The mother liquors were concentrated in vacuo and the residue dissolved in EtOAc (10 mL). Dilution with cyclohexane (90 ml) precipitated a second batch of product which was recovered by filtration. The two batches were combined as an ethyl acetate solution and concentrated in vacuo to afford the title compound as a fawn solid (16.65 g).

LCMS (Method 2): Rt=3.22 min, m/z 243 [M+H]+

Intermediate 1B. 5-methyl-1-[3-(trifluoromethyl) phenyl]-1H-imidazol-2(3H)-one

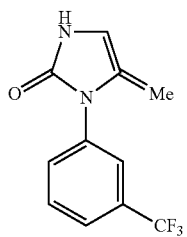

A solution of 1-(prop-2-ynyl)-3-[3-(trifluoromethyl)phenyl]urea (intermediate 1A) (11.2 g, 46 mmol) in THF (60 mL) and acetonitrile (120 mL) was added, under a nitrogen atmosphere, to a stirred suspension of sodium hydride (60% dispersion in mineral oil) (4.62 g, 115 mmol) in THF (60 mL) at such a rate that gas evolution was not over-vigorous and the internal temperature remained below 30° C. The mixture was stirred at RT for 2.5 h, a thick precipitate having formed within 1 h. The reaction mixture was cautiously quenched with water (15 mL) and the resulting solution was treated with 1 M hydrochloric acid (150 mL, 150 mmol). The mixture was stirred for 4 hours then allowed to stand for 15 hours. Saturated brine (150 mL) was added and the phases were partitioned. The aqueous phase was extracted with EtOAc (100 mL). The combined organic phase was washed with saturated brine (100 mL), dried (sodium sulfate) and concentrated in vacuo. The residue was triturated with EtOAc (33 mL). The resultant solid was taken into DCM and filtered. The filtrate was concentrated in vacuo to afford the title compound (10.0 g) as a fawn solid.

LCMS (Method 1): Rt=2.63 min, m/z 243 [M+H]+

Intermediate 1C. 2-ethoxy-5-methyl-1-[3-(trifluoromethyl)phenyl]-1H-imidazole

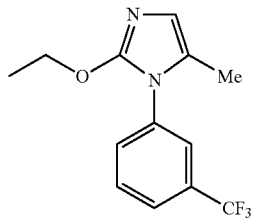 [SMILES: CCOc1ncc(C)n1-c1cccc(C(F)(F)F)c1]

A solution of triethyloxonium tetrafluoroborate (9.0 g, 47 mmol) in DCM (62 mL) was added to a stirred solution of 5-methyl-1-[3-(trifluoromethyl)phenyl]-1H-imidazol-2 (3H)-one (Intermediate 1B, 9.0 g, 37 mmol) in DCM (124 mL) under a nitrogen atmosphere. The solution was stirred at RT for 2.5 h then treated with water (50 mL) then 1 M sodium hydroxide (50 mL). The phases were partitioned. The aqueous phase was washed with DCM (2×50 mL). The combined organic phase was dried (sodium sulfate). The solution of the crude product was filtered through 2×50 g flash SCX 2 cartridges. Each cartridge was rinsed with 10% methanol in DCM (100 mL) then the product fraction was eluted with 2M methanolic ammonia solution (100 mL). The fractions recovered with methanolic ammonia were combined and concentrated in vacuo to afford the title compound (7.92 g) as a brown solid.

LCMS (Method 1): Rt=2.41 min, m/z 271 [M+H]

Intermediate 1D. 4-bromo-2-ethoxy-5-methyl-1-[3-(trifluoromethyl)phenyl]-1H-imidazole

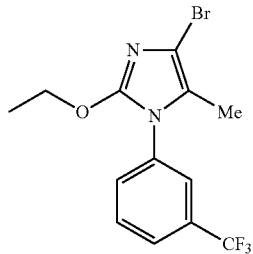

A solution of NBS (5.16 g, 29 mmol) in MeCN (60 mL) was added to a stirred solution of 2-ethoxy-5-methyl-1-[3-(trifluoromethyl)phenyl]-1H-imidazole (Intermediate 1C, 7.92 g, 29 mmol) in MeCN (115 mL) at such a rate that the internal temperature of the mixture did not exceed 25° C. (a RT cooling bath was used). After 0.5 h the mixture was diluted with water (50 mL) and saturated sodium carbonate (aq) (50 mL). Ethyl acetate (50 mL) was added. The mixture was stirred vigorously then the phases were separated. The organic phase was washed with saturated brine (50 mL), dried (sodium sulfate) and concentrated in vacuo. The residue was taken into dichloromethane and filtered through a 25 g Si II SPE cartridge. The cartridge was washed with DCM and 10% EtOAc in DCM. The filtrate was concentrated in vacuo to afford the title compound as an off-white solid (8.93 g).

LCMS (Method 1): Rt=3.86 min, m/z 349 [M($^{79}$Br)+H]+

Intermediate 1E. 4-(2-bromo-1H-imidazol-1-yl)benzonitrile

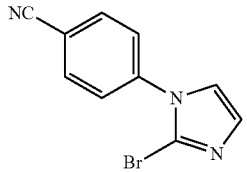 [SMILES: N#Cc1ccc(-n2ccnc2Br)cc1]

4-Imidazol-1-yl-benzonitrile (5.0 g, 29.6 mmol) was dissolved in dioxane and N-bromosuccinimide (5.26 g, 29.6 mmol) was added. The solution was heated at 60° C. for 2 h. The solution was decanted from a gummy residue and evaporated to give a yellow solid. This was triturated with EtOAc to give a cream solid which was further purified by chromatography using EtOAc as eluant to afford Intermediate 1E (0.79 g) as a pale yellow solid.

LCMS (Method 1) Rt=2.44 min., m/z 248 and 250 (Br isotopes)

Intermediate 1F. 4-{2'-ethoxy-5'-methyl-1'-[3-(trifluoromethyl)phenyl]-1H,1'H-[2,4'-biimidazol]-1-yl}benzonitrile

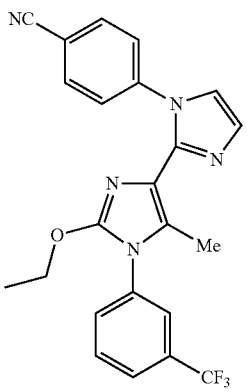 [SMILES: CCOc1nc(-c2nccn2-c2ccc(C#N)cc2)c(C)n1-c1cccc(C(F)(F)F)c1]

2-Dicyclohexylphosphino-2',4',6'-triisopropylbiphenyl (19 mg, 0.04 mmol), (2-dicyclohexylphosphino-2',4',6'-triisopropyl-1,1'-biphenyl)palladium(II) dichloride (15.7 mg, 0.02 mmol), tetrahydroxydiboron (270 mg, 3 mmol) and potassium acetate (294 mg, 3 mmol) were mixed in a nitrogen filled vial. A solution of 4-bromo-2-ethoxy-5-methyl-1-[3-(trifluoromethyl)phenyl]-1H-imidazole (Intermediate 1D, 349 mg, 1 mmol) in IMS (10 ml) was added and the solution heated at 80° C. for 2 h. A solution of $K_2CO_3$ (1.8M, 1.66 ml) was added followed by a suspension of 4-(2-bromo-1H-imidazol-1-yl)benzonitrile (Intermediate 1E, 248 mg, 1 mmol) in THF. Heating was continued overnight at 80° C. After cooling, the mixture was filtered through celite, washing with EtOAc, and evaporated to dryness. The residue was extracted into EtOAc, decanted, dried over $Na_2SO_4$ filtered and evaporated. Purification was performed by silica gel chromatography eluting with 20% to 100% EtOAc-cyclohexane. The third eluted component was the title compound (91 mg, 21%).

LCMS (Method 2) Rt=2.73 min., m/z 438.3

Intermediate 1G. 4-{5'-methyl-2'-oxo-1'-[3-(trifluoromethyl)phenyl]-2',3'-dihydro-1H, 1'H-[2,4'-biimidazol]-1-yl}benzonitrile

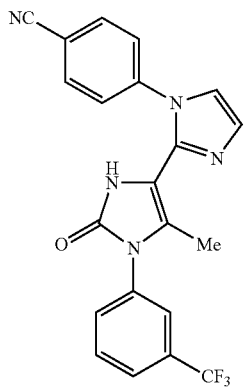 [SMILES: Cc1c(-c2nccn2-c2ccc(C#N)cc2)[nH]c(=O)n1-c1cccc(C(F)(F)F)c1]

4-{2'-ethoxy-5'-methyl-'-[3-(trifluoromethyl)phenyl]-1H,1'H-[2,4'-biimidazol]-1-yl}benzonitrile (Intermediate 1F, 170 mg, 0.39 mmol), acetone (5 ml) and 1M HCl (3 ml) were heated together at 60° C. for 3.5 h. Concentrated HCl (0.5 ml) was added and heating continued overnight. The mixture was cooled and most of the acetone removed by evaporation. The solution was basified with aqueous $NaHCO_3$ and the white solid title compound filtered off and dried at 50° C. Yield 150 mg (94%).

LCMS (Method 3): Rt=3.61 min, m/z 410.1 [M+H]+
$^1$H NMR (400 MHz, d6-DMSO): δ 10.47 (1H, s), 8.05-7.99 (2H, m), 7.79-7.73 (3H, m), 7.72 (1H, d, J=1.4 Hz), 7.68-7.63 (1H, m), 7.63-7.58 (2H, m), 7.28 (1H, d, J=1.4 Hz), 1.70 (3H, s).

Intermediate 1H. 1-(4-cyanophenyl)-N-cyclopentyl-5'-methyl-2'-oxo-1'-[3-(trifluoromethyl)phenyl]-1',2'-dihydro-1H,3'H-[2,4'-biimidazole]-3'-carboxamide

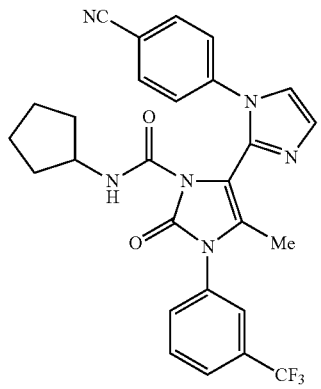 [SMILES: Cc1c(-c2nccn2-c2ccc(C#N)cc2)n(C(=O)NC2CCCC2)c(=O)n1-c1cccc(C(F)(F)F)c1]

4-{5'-methyl-2'-oxo-1'-[3-(trifluoromethyl)phenyl]-2',3'-dihydro-1H,1'H-[2,4'-biimidazol]-1-yl}benzonitrile (Intermediate 1G, 108 mg, 0.26 mmol) was suspended in dry DCM (5 ml) and DIPEA (130 µl, 3 eq.) was added followed by cyclopentyl isocyanate (90 µl, 88 mg, 0.79 mmol). The mixture was heated and stirred at 45° C. for 24 h. The solvent was removed in vacuo and the residue purified by chromatography eluting with EtOAc, thereby yielding Intermediate 8 (100 mg, 73%).

LCMS (Method 3): Rt=4.55 min, m/z 521.2 [M+H]+

¹H NMR (400 MHz, d6-DMSO): δ 8.13 (1H, d, J=6.8 Hz), 8.02-7.98 (1H, m), 7.98-7.93 (2H, m), 7.91-7.77 (3H, m), 7.72 (1H, d, J=1.4 Hz), 7.57-7.51 (2H, m), 7.20 (1H, d, J=1.4 Hz), 3.75-3.65 (1H, m), 1.90 (3H, s), 1.75-1.57 (2H, m), 1.56-1.40 (4H, m), 1.35-0.94 (2H, m).

1-(4-Cyanophenyl)-2-{3-(cyclopentylcarbamoyl)-5-methyl-2-oxo-1-[3-(trifluoromethyl)phenyl]-2,3-dihydro-1H-imidazol-4-yl}-3-methyl-1H-imidazol-3-ium benzene sulfonate Intermediate 1H (100 mg, 0.192 mmol) was stirred in THF (2 ml) and methyl benzenesulfonate (39.6 mg, 0.23 mmol) was added. Stirring was continued at RT for 1.5 h then heated at 50° C. for 2 h, left to stand overnight at RT, heated at 50° C. for a further 6 h, finally allowed to stand at RT for 3 days. Diethyl ether was added and the resulting white precipitate was separated from the supernatant, dissolved in MeCN-water and freeze dried to give title compound as a white solid (135 mg).

LCMS (Method 3): Rt=4.04 min, m/z 535.3 [M]+

¹H NMR (400 MHz, d6-DMSO): δ8.38 (1H, d, J=2.1 Hz), 8.23 (1H, d, J=6.4 Hz), 8.22 (1H, d, J=2.1 Hz), 8.15-8.09 (2H, m), 7.97-7.89 (2H, m), 7.86-7.77 (2H, m), 7.71-7.66 (2H, m), 7.62-7.56 (2H, m), 7.35-7.26 (3H, m), 3.95-3.85 (1H, m), 3.92 (3H, s), 1.88 (3H, s), 1.85-1.72 (2H, m), 1.62-1.50 (4H, m), 1.46-1.26 (2H, m).

Example 2. 1-(4-Cyanophenyl)-2-{3-(cyclopentylcarbamoyl)-5-methyl-2-oxo-1-[3-(trifluoromethyl)phenyl]-2,3-dihydro-1H-imidazol-4-yl}-3-benzyl-1H-imidazol-3-ium bromide

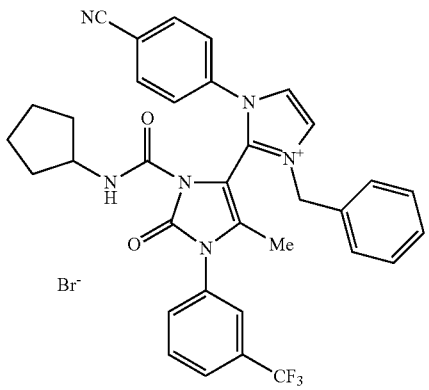 [SMILES: Cc1c(-c2n(-c3ccc(C#N)cc3)cc[n+]2Cc2ccccc2)n(C(=O)NC2CCCC2)c(=O)n1-c1cccc(C(F)(F)F)c1 ; [Br-]]

Intermediate 1H (70 mg, 0.135 mmol) and benzyl bromide (50 μl, 70 mg, 0.41 mmol) were heated in THF (1 ml) at 50° C. overnight. Diethyl ether was added and the precipitated solid was washed with diethyl ether and dried (66 mg, 71%).

LCMS (Method 3): Rt=4.38 min, m/z 611.3 [M]+

¹H NMR (400 MHz, d6-DMSO): δ8.43 (1H, d J=2.2 Hz), 8.26 (1H, d J=2.2 Hz), 8.19 (1H, d J=6.9 Hz), 8.12 (2H, d J=8.8 Hz), 7.96-7.90 (2H, m), 7.86-7.76 (2H, m), 7.71 (2H, d J=8.8 Hz), 7.44-7.34 (5H, m), 5.60 (1H, d J=14.9 Hz), 5.47 (1H, d J=14.9 Hz), 3.90-3.80 (1H, m), 1.90-1.70 (5H, m), 1.65-1.46 (4H, m), 1.45-1.25 (2H, m).

The following compounds were prepared by analogous procedures to that used in Example 1. In the table below where rotameric signals have been identified in the NMR spectrum these have been labelled by *.

| Ex | Structure | Isocyanate | 1H NMR | LC-MS Method 3 |
|---|---|---|---|---|
| 3 | (structure shown) | Isocyanato-cyclobutane | ¹H NMR (400 MHz, d6-DMSO): δ 8.43 (1H, d, J = 7.6 Hz), 8.37 (1H, d, J = 2.1 Hz), 8.21 (1H, d, J = 2.1 Hz), 8.14-8.09 (2H, m), 7.96-7.91 (2H, m), 7.86-7.77 (2H, m), 7.70-7.65 (2H, m), 7.61-7.58 (2H, m), 7.35-7.30 (3H, m), 4.12-4.02 (1H, m), 3.91 (3H, s), 2.20-2.10 (2H, m), 2.03-1.83 (2H, m), 1.87 (3H, s), 1.68-1.56 (2H, m) | Rt = 3.81 min, m/z = 521.2 [M]+ |

| Ex | Structure | Isocyanate | 1H NMR | LC-MS Method 3 |
|---|---|---|---|---|
| 4 | 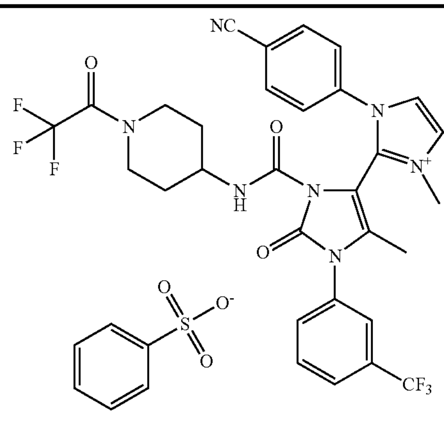 | 2,2,2-Trifluoro-1-(4-isocyanato-piperidin-1-yl)-ethanone | $^1$H NMR (400 MHz, d6-DMSO): δ 8.40-8.35 (1H, m), 8.22 (1H, d J = 2.1 Hz), 8.15-8.10 (2H, m), 7.97-7.90 (2H, m), 7.86-7.76 (2H, m), 7.69 (2H, d J = 8.7 Hz), 7.62-7.56 (2H, m), 7.34-7.26 (3H, m), 4.18-4.08 (1H, m), 3.96-3.90 (3H, 2xbr s)*, 3.88-3.72 (2H, m), 3.36-3.28 signals obscured by water, 3.04 (1H, appt J = 11.5 Hz), 1.92-1.74 (5H, overlapping m and S), 1.62-1.38 (2H, m) | Rt = 3.92 min, m/z = 646.4 [M]+ |
| 5 | 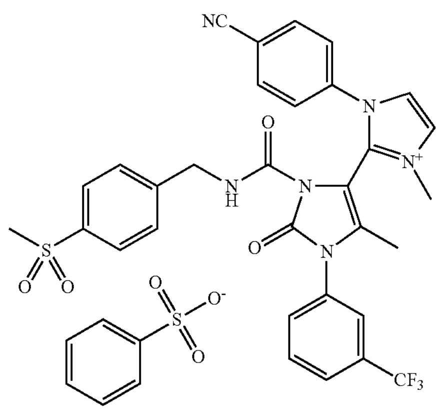 [SMILES: Cc1c(-c2n(-c3ccc(C#N)cc3)cc[n+]2C)n(C(=O)NCc2ccc(S(C)(=O)=O)cc2)c(=O)n1-c1cccc(C(F)(F)F)c1 ; O=S(=O)([O-])c1ccccc1] | 1-Isocyanatomethyl-4-methane-sulfonyl-benzene | $^1$H NMR (400 MHz, d6-DMSO): δ 8.96 (1H, t J = 6.1 Hz), 8.34 (1H, d J = 2.1 Hz), 8.20 (1H, d J = 2.1 Hz), 8.06 (2H, d J = 8.8 Hz), 7.98-7.78 (6H, m), 7.65-7.57 (4H, m), 7.46 (2H, d J = 8.4 Hz), 7.34-7.27 (3H, m), 4.44 ((2H, d J = 6.1 Hz), 3.90 (3H, s), 3.22 (3H, s), 1.89 (3H, s) | Rt = 3.54 min, m/z = 635.3 [M]+ |

Example 6. 1-(4-Cyano-phenyl)-5-[3-cyclopentyl-carbamoyl-5-methyl-2-oxo-1-(3-trifluoromethyl-phenyl)-2,3-dihydro-1H-imidazol-4-yl]-4-methyl-1H-[1,2,4]triazol-4-ium benzene sulfonate Intermediate 6A.
4-(5-Bromo-[1,2,4]triazol-1-yl)-benzonitrile

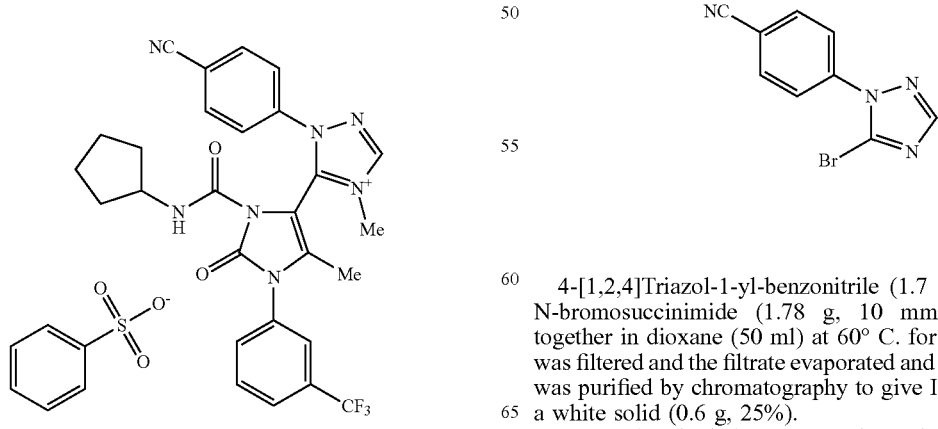

4-[1,2,4]Triazol-1-yl-benzonitrile (1.7 g, 10 mmol) and N-bromosuccinimide (1.78 g, 10 mmol) were heated together in dioxane (50 ml) at 60° C. for 3 h. The mixture was filtered and the filtrate evaporated and the resulting solid was purified by chromatography to give Intermediate 13 as a white solid (0.6 g, 25%).

LCMS (Method 3) Rt=2.61 min., m/z 249 and 251 (Br isotopes)

Intermediate 6B. 4-{5-[2-Ethoxy-5-methyl-1-(3-trifluoromethyl-phenyl)-1H-imidazol-4-yl]-[1,2,4]triazol-1-yl}-benzonitrile

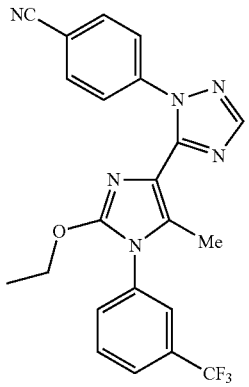

4-Bromo-2-ethoxy-5-methyl-1-[3-(trifluoromethyl)phenyl]-1H-imidazole (Intermediate 1D, 349 mg, 1 mmol), 2-dicyclohexylphosphino-2',4',6'-triisopropylbiphenyl (19 mg, 0.04 mmol), (2-dicyclohexylphosphino-2',4',6'-triisopropyl-1,1'-biphenyl)palladium(II) dichloride (15.7 mg, 0.02 mmol), tetrahydroxydiboron (270 mg, 3 mmol) and potassium acetate (294 mg, 3 mmol) and IMS (10 ml) were sealed in each of 2 vials under $N_2$ and heated at 80° C. for 1.5 h, then 4-(5-bromo-[1,2,4]triazol-1-yl)-benzonitrile (Intermediate 6A, 249 mg, 1 mmol) and 1.8M $K_2CO_3$ (1.66 ml) were added to each vial and heating continued for a further 1 h. The reactions were combined, filtered and evaporated and the residue triturated with DCM to remove more inorganic solids. The solution was chromatographed on silica (0% to 50% EtOAc-DCM) to provide Intermediate 6B (100 mg, 11.5%).

LCMS (Method U2) Rt=1.55 min., m/z 439.2

Intermediate 6C. 4-{5-[5-Methyl-2-oxo-1-(3-trifluoromethyl-phenyl)-2,3-dihydro-1H-imidazol-4-yl]-[1,2,4]triazol-1-yl}-benzonitrile

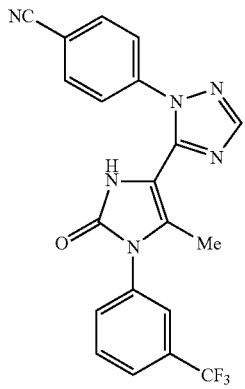

4-{5-[2-Ethoxy-5-methyl-1-(3-trifluoromethyl-phenyl)-1H-imidazol-4-yl]-[1,2,4]triazol-1-yl}-benzonitrile (Intermediate 6B, 130 mg, 0.30 mmol), acetone (4 ml) and 5M HCl (3 ml) were heated together at 60° C. for 2 h and allowed to cool. The acetone was removed in vacuo and the aqueous solution basified with $NaHCO_3$ solution. The white solid Intermediate 6C was filtered off, washed with water and dried (79 mg, 66%).

LCMS (Method U2) Rt=1.33 min., m/z 411.1

Intermediate 6D. 5-[2-(4-Cyano-phenyl)-2H-[1,2,4]triazol-3-yl]-4-methyl-2-oxo-3-(3-trifluoromethyl-phenyl)-2,3-dihydro-imidazole-1-carboxylic acid cyclopentylamide

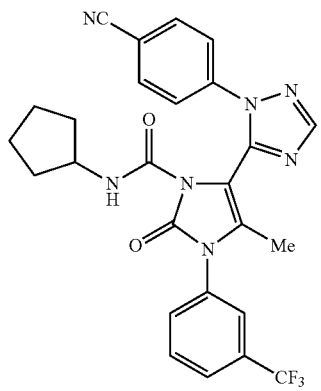 [SMILES: Cc1c(-c2ncnn2-c2ccc(C#N)cc2)n(C(=O)NC2CCCC2)c(=O)n1-c1cccc(C(F)(F)F)c1]

4-{5-[5-Methyl-2-oxo-1-(3-trifluoromethyl-phenyl)-2,3-dihydro-1H-imidazol-4-yl]-[1,2,4]triazol-1-yl}-benzonitrile (Intermediate 6C, 79 mg, 0.192 mmol), cyclopentyl isocyanate (58 μl, 0.58 mmol) and DIPEA (101 μl, 0.58 mmol) were stirred in DCM (4 ml) at 45° C. overnight. Solvent was evaporated and the product was purified by silica gel chromatography (50% to 100% EtOAc-cyclohexane) to give Intermediate 6D as a white solid (73 mg, 73%).

LCMS (Method 3): Rt=5.16 min, m/z 522.3 [M+H]+

$^1$H NMR (400 MHz, CDCl$_3$): δ 8.27 (1H, d, J=6.8 Hz), 8.19 (1H, s), 7.81-7.74 (3H, m), 7.70 (1H, tm, J=8 Hz), 7.67-7.63 (2H, m), 7.61 (1H, m), 7.52 (1H, dm, J=8 Hz), 3.98-3.87 (1H, m), 1.93 (3H, s), 1.91-1.73 (2H, m), 1.69-1.52 (5H, m), 1.47-1.35 (1H, m).

1-(4-Cyano-phenyl)-5-[3-cyclopentylcarbamoyl-5-methyl-2-oxo-1-(3-trifluoromethyl-phenyl)-2,3-dihydro-1H-imidazol-4-yl]-4-methyl-1H-[1,2,4]triazol-4-ium benzene sulfonate Intermediate 6D (50 mg, 0.096 mmol) and methyl benzenesulphonate (18 μl) were stirred and heated in THF (2 ml) at 50° C. for 3 days. Diethyl ether was added and the supernatant decanted from the gummy residue. The residue was washed with ether, taken up in MeCN-water and freeze dried to give the title compound as a white solid (40 mg, 60%).

LCMS (Method 3): Rt=4.13 min, m/z 536.3 [M]+

$^1$H NMR (400 MHz, d6-DMSO): δ 8.68 (1H, s), 8.20 (1H, d, J=7.2 Hz), 8.16-8.11 (2H, m), 7.98 (1H, m), 7.97-7.93 (1H, dm), 7.89-7.84 (4H, m), 7.61-7.58 (2H, m), 7.35-7.27 (3H, m), 3.98 (3H, s), 3.91-3.81 (1H, m), 1.91 (3H, s), 1.85-1.66 (2H, m), 1.65-1.36 (5H, m), 1.33-1.20 (1H, m).

Example 7. 3-(4-Cyano-phenyl)-2-[4-cyclopentyl-carbamoyl-2-methyl-5-oxo-1-(3-trifluoromethyl-phenyl)-2,5-dihydro-1H-pyrazol-3-yl]-1-methyl-3H-imidazol-1-ium benzenesulfonate

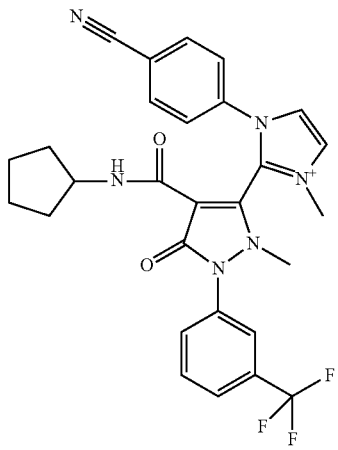 [SMILES: Cn1c(-c2n(-c3ccc(C#N)cc3)cc[n+]2C)c(C(=O)NC2CCCC2)c(=O)n1-c1cccc(C(F)(F)F)c1]

Intermediate 7A.
1-(4-Cyano-phenyl)-1H-imidazole-2-carboxylate lithium salt

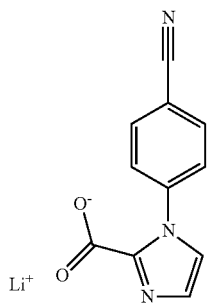 [SMILES: [Li+] ; N#Cc1ccc(-n2ccnc2C(=O)[O-])cc1]

A solution of n-butyl lithium (1.38 mL of a 1.6 M solution in hexanes, 2.2 mmol) was added dropwise to a cold (−75° C.) solution of 4-imidazol-1-yl-benzonitrile in THF (10 ml) in an argon purged flask. The addition was at such a rate that the internal temperature did not exceed −70° C. The mixture was stirred at −75° C. for 1 h and the resultant orange suspension was poured onto ca. 3 g of ground dry ice. The resultant mixture was stirred for 1 h, a thick white precipitate forming over time. The solvent was evaporated in vacuo and the residue was triturated with diethyl ether (15 mL). The solid was recovered by filtration and dried in vacuo to afford Intermediate 7A (429 mg, 1.96 mmol).

$^1$H NMR (400 MHz, d6-DMSO): δ 7.90 (2H, d, J=8.7 Hz), 7.59 (2H, d, J=8.7 Hz), 7.33 (1H, d, J=1.3 Hz), 6.97 (1H, d, J=1.3 Hz).

Intermediate 7B.
1-(4-Cyano-phenyl)-1H-imidazole-2-carboxylic acid methyl ester

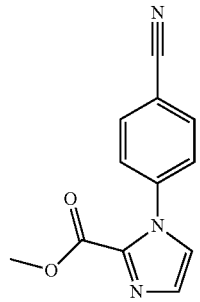 [SMILES: COC(=O)c1nccn1-c1ccc(C#N)cc1]

Iodomethane (1.13 mL, 18.1 mmol) was added to a vigorously stirred mixture of Intermediate 7A (3.18 g, 14.5 mmol) and DMF (45 mL). The mixture was stirred for 18 h and the resultant solution was poured into 1:1 saturated brine:water (450 ml). The mixture was extracted with ethyl acetate (4×50 mL). The combined organic phase was dried (sodium sulfate) and concentrated in vacuo to afford Intermediate 7B (1.40 g, 6.7 mmol) as a white solid.

LCMS (Method U2) Rt=0.98 min, m/z 228.2 [M+H]+.

Intermediate 7C. 1-(4-Cyano-phenyl)-1H-imidazole-2-carboxylic acid N'-(3-trifluoromethyl-phenyl)-hydrazide

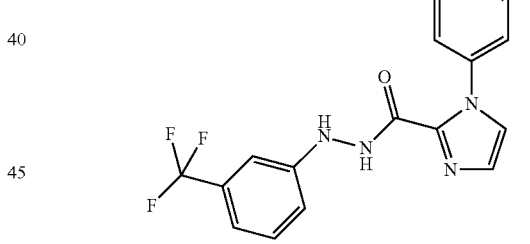

A mixture of 3-trifluoromethyl-phenylhydrazine hydrochloride (1.98 g, 9.3 mmol) and bis(trimethylaluminium)-1,4-diazabicyclo[2.2.2]octane adduct (2.38 g, 9.3 mmol) in dry THF (30 mL) was stirred at 40° C. for 1 h. A suspension of Intermediate 7B (1.40 g, 6.7 mmol) in dry THF (35 mL) was added and the mixture then heated at reflux for 16 h. After allowing to cool to ambient temperature the mixture was quenched by cautious dropwise addition with 4M hydrochloric acid (3.0 mL) and stirred vigorously for 5 minutes then made basic by addition of 5% aqueous potassium carbonate solution (30 mL). The mixture was diluted with water (30 mL) and extracted with ethyl acetate (3×30 mL). The combined organic phase was washed with brine (30 mL), dried (sodium sulfate) and concentrated in vacuo. The residue was purified by flash column chromatography (80 g Si column eluted with 0-25% ethyl acetate in DCM) to afford Intermediate 7C (2.03 g, 5.47 mmol) as a yellow foam.

LCMS (Method U2) Rt=1.39 min, m/z 372.2 [M+H]+.

Intermediate 7D. Bis-BOC-protected-1-(4-cyano-phenyl)-1H-imidazole-2-carboxylic acid N'-(3-trifluoromethyl-phenyl)-hydrazide

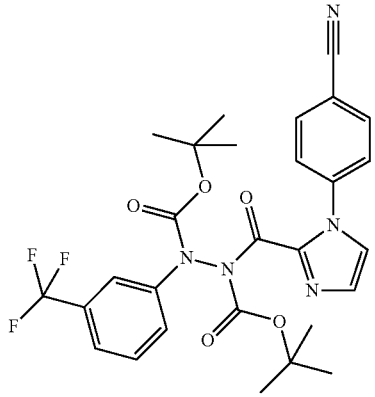 [SMILES: CC(C)(C)OC(=O)N(C(=O)c1nccn1-c1ccc(C#N)cc1)N(C(=O)OC(C)(C)C)c1cccc(C(F)(F)F)c1]

4-Dimethylamino-pyridine (33 mg, 0.27 mmol) was added to a mixture of Intermediate 7C (2.03 g, 5.47 mmol), di-tert-butyl dicarbonate (1.91 g, 8.75 mmol), trimethylamine (1.90 mL, 13.68 mmol) and dry THF (40 mL). The mixture was heated at 50° C. for 60 h. The mixture was concentrated in vacuo and the residue was purified by flash column chromatography (40 g silica cartridge eluted with 0-40% ethyl acetate in pentane) to afford Intermediate 7D (2.36 g, 4.13 mmol) as a white solid.

LCMS (Method U2) Rt=1.74 min, m/z 572.3 [M+H]+.

Intermediate 7E. N'-[1-(4-Cyano-phenyl)-1H-imidazole-2-carbonyl]-N-(3-trifluoromethyl-phenyl)-hydrazinecarboxylic acid tert-butyl ester

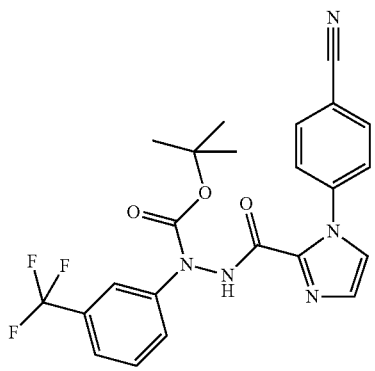 [SMILES: CC(C)(C)OC(=O)N(NC(=O)c1nccn1-c1ccc(C#N)cc1)c1cccc(C(F)(F)F)c1]

Magnesium perchlorate (177 mg, 0.79 mmol) was added to a solution of Intermediate 7D (2.36 g, 4.13 mmol) in dry acetonitrile (60 mL). The mixture was stirred and heated at 50° C. for 2 h. The cold mixture was concentrated to a small volume and diluted with saturated aqueous sodium hydrogen carbonate solution (25 mL). The mixture was extracted with ethyl acetate (3×25 mL). The combined organic phase was dried (sodium sulfate) and concentrated in vacuo to afford Intermediate 7E (1.99 g, ca. quant.) as a yellow foam.

LCMS (Method U2) Rt=1.61 min, m/z 472.2 [M+H]+.

Intermediate 7F. N'-[1-(4-Cyano-phenyl)-1H-imidazole-2-carbonyl]-N'-methyl-N-(3-trifluoromethyl-phenyl)-hydrazinecarboxylic acid tert-butyl ester

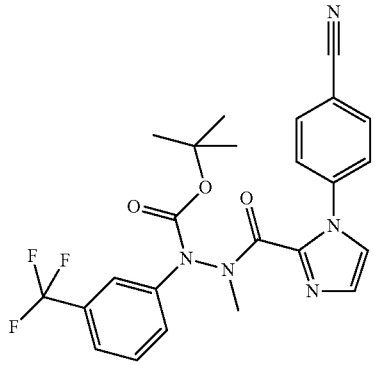 [SMILES: CN(C(=O)c1nccn1-c1ccc(C#N)cc1)N(C(=O)OC(C)(C)C)c1cccc(C(F)(F)F)c1]

Sodium hydride (110 mg of a 60% dispersion in mineral oil, 2.76 mmol) was added to a solution of Intermediate 7E (1.00 g, 2.12 mmol) in dry DMF (20 mL). The mixture was stirred for 1 h then treated with iodomethane (175 μL, 2.82 mmol). The mixture was stirred for 2 h then diluted with brine:water 2:1 (200 mL). The mixture was extracted with ethyl acetate (3×25 mL). The combined organic phase was dried (sodium sulfate) and concentrated in vacuo. The residue was purified by flash column chromatography (40 g Si cartridge eluted with 0-10% ethyl acetate in DCM) to afford Intermediate 7F (0.82 g, 1.69 mmol) as a white foam.

LCMS (Method U2) Rt=1.63 min, m/z 486.2 [M+H]+.

Intermediate 7G. 1-(4-Cyano-phenyl)-1H-imidazole-2-carboxylic acid N-methyl-N'-(3-trifluoromethyl-phenyl)-hydrazide

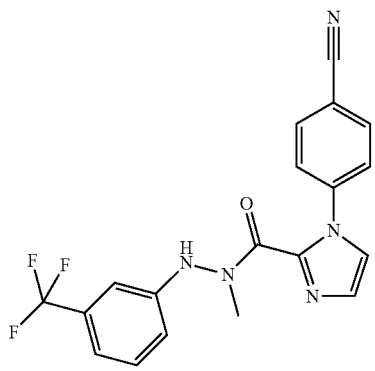 [SMILES: CN(Nc1cccc(C(F)(F)F)c1)C(=O)c1nccn1-c1ccc(C#N)cc1]

A mixture of Intermediate 7F (0.82 g, 1.69 mmol) and 4M hydrogen chloride in dioxane (4.2 mL, 16.9 mmol) was stirred for 2 h then concentrated in vacuo. The residue was passed through a 20 g SCX-2 cartridge washing with dichloromethane then dichloromethane methanol and eluting with 2M methanolic ammonia in dichloromethane. Concentration of the appropriate fractions gave the crude product which was further purified by flash column chromatography (40 g Si cartridge eluted with 0-4% 2M methanolic ammonia in dichloromethane) to afford Intermediate 7G (569 mg, 1.48 mmol) as an off white foam.

LCMS (Method U2) Rt=1.35 min, m/z 386.2 [M+H]+.

Intermediate 7H. 3-[N'-[1-(4-Cyano-phenyl)-1H-imidazole-2-carbonyl]-N'-methyl-N-(3-trifluoromethyl-phenyl)-hydrazino]-3-oxo-propionic acid ethyl ester

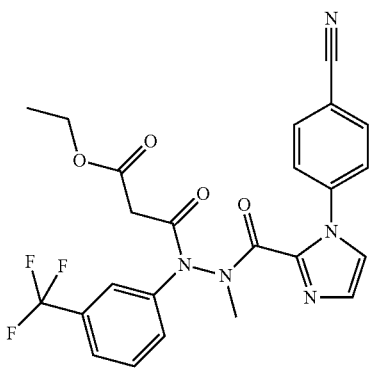 [SMILES: CCOC(=O)CC(=O)N(c1cccc(C(F)(F)F)c1)N(C)C(=O)c1nccn1-c1ccc(C#N)cc1]

A mixture of Intermediate 7G (569 mg, 1.48 mmol), ethyl malonyl chloride (0.202 mL, 1.63 mmol), pyridine (0.144 mL, 1.78 mmol), 4-dimethylamino-pyridine (9 mg, 0.07 mmol) and dry tetrahydrofuran (15 mL) was stirred at 50° C. A further aliquot of ethyl malonyl chloride (0.208 mL, 1.63 mmol) and pyridine (0.144 mL, 1.78 mmol) were added after 16 h. Heating was discontinued after a further 3 h. The mixture was concentrated in vacuo. The residue was taken into ethyl acetate (30 mL) and washed with saturated aqueous sodium hydrogen carbonate (25 mL) and brine (25 mL) then dried (sodium sulfate) and concentrated in vacuo. The residue was purified by flash column chromatography (40 g Si cartridge eluted with 0-25% ethyl acetate in DCM) to afford Intermediate 7H (0.51 g, 1.02 mmol) as a white foam.

LCMS (Method U2) Rt=1.48 min, m/z 500.2 [M+H]+.

Intermediate 7I. 5-[1-(4-Cyano-phenyl)-1H-imidazol-2-yl]-1-methyl-3-oxo-2-(3-trifluoromethyl-phenyl)-2,3-dihydro-1H-pyrazole-4-carboxylic acid ethyl ester

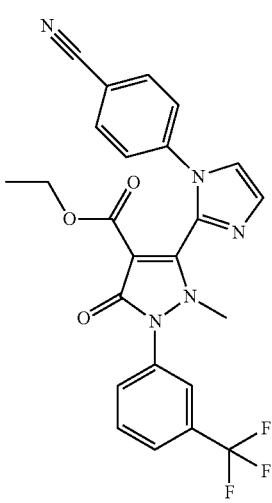 [SMILES: CCOC(=O)c1c(-c2nccn2-c2ccc(C#N)cc2)n(C)n(-c2cccc(C(F)(F)F)c2)c1=O]

Sodium ethoxide (120 mg, 1.76 mmol) was added to a stirred suspension of Intermediate 7H (440 mg, 0.88 mmol) in absolute ethanol (8 mL). The mixture was stirred at RT for 16 h. A second aliquot of sodium ethoxide (30 mg, 0.44 mmol) was added and the mixture was heated at 40° C. for 3 h. The cold mixture was diluted with water (10 mL) and extracted with ethyl acetate (15 mL). The organic phase was washed with 10% aqueous citric acid (15 mL). The aqueous phases were combined and extracted with ethyl acetate (10 mL). The combined organic phase was dried (sodium sulfate) and concentrated in vacuo. The residue was purified by flash column chromatography (25 g Si cartridge eluted with 0-100% ethyl acetate in dichloromethane) to afford Intermediate 7I (372 mg, 0.77 mmol) as a white solid.

LCMS (Method U2) Rt=1.24 min, m/z 482.2 [M+H]+.

Intermediate 7J. 5-[1-(4-Cyano-phenyl)-1H-imidazol-2-yl]-1-methyl-3-oxo-2-(3-trifluoromethyl-phenyl)-2,3-dihydro-1H-pyrazole-4-carboxylic acid

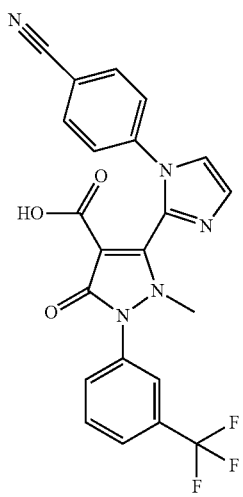

A solution of lithium hydroxide hydrate (162 mg, 3.86 mmol) in water (5 mL) was added to a solution of Intermediate 7I (372 mg, 0.77 mmol) in tetrahydrofuran (16 mL). The mixture was stirred at RT for 21 h. The mixture was then treated with 5% aqueous potassium hydrogen sulfate solution (20 mL) and extracted with ethyl acetate (2×15 mL). The combined organic phase was washed with brine (15 mL), dried (sodium sulfate) and concentrated in vacuo to afford Intermediate 7J (350 mg, ca quantitative) as a white solid.

LCMS (Method U2) Rt=1.17 min, m/z 454.1 [M+H]+.

Intermediate 7K. 5-[1-(4-Cyano-phenyl)-1H-imidazol-2-yl]-1-methyl-3-oxo-2-(3-trifluoromethyl-phenyl)-2,3-dihydro-1H-pyrazole-4-carboxylic acid cyclopentyl-amide

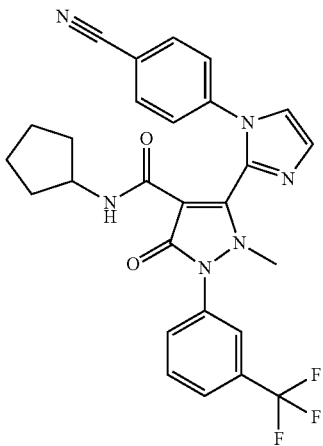 [SMILES: Cn1c(-c2nccn2-c2ccc(C#N)cc2)c(C(=O)NC2CCCC2)c(=O)n1-c1cccc(C(F)(F)F)c1]

Carbonyl diimidazole (53 mg, 0.325 mmol) was added to a suspension of Intermediate 7J (113 mg, 0.25 mmol) in dry tetrahydrofuran (2.0 mL). The mixture was stirred at RT for 2 h then cyclopentyl amine (49 µL, 0.5 mmol) was added. The mixture was stirred for 1 h. The resultant solution was diluted with ethyl acetate (25 mL) and washed with water (2×10 mL) then brine (10 mL). The organic phase was dried (sodium sulfate) and concentrated in vacuo. The residue was purified by flash column chromatography (2 g Si-II column eluted ethyl acetate) to afford the Intermediate 7K (100 mg, 0.19 mmol) as a white solid.

$^1$H NMR (400 MHz, CDCl3): δ 7.95 (1H, d J=7.2 Hz), 7.76-7.58 (6H, m), 7.47 (1H, d, J=1.3 Hz), 7.43-7.38 (3H, m), 4.04-3.94 (1H, m), 3.37 (3H, s), 1.88-1.72 (2H, m), 1.68-1.46 (4H, m), 1.42-1.30 (1H, m), 1.24-1.14 (1H, m).

LCMS (Method 3): Rt=4.50 min, m/z 521.3 [M+H]+

3-(4-Cyano-phenyl)-2-[4-cyclopentylcarbamoyl-2-methyl-5-oxo-1-(3-trifluoromethyl-phenyl)-2,5-dihydro-1H-pyrazol-3-yl]-1-methyl-3H-imidazol-1-ium benzenesulfonate Methyl benzenesulfonate (28 µL, 0.20 mmol) was added to a solution of Intermediate 7K (75 mg, 0.14 mmol) in dichloromethane (1.0 mL). The mixture was heated at 35° C. for 18 h. A second aliquot of methyl benzenesulfonate (100 µL, 0.75 mmol) was added and heating was continued for 48 h, most of the solvent was lost. The mixture was cooled to afford the crude product. This was purified by flash column chromatography (1 g Si column eluted with 2%, 10% then 20% methanol in dichloromethane). The product thus obtained was freeze-dried from acetonitrile/water to afford the title compound; (95 mg, 0.128 mmol) as a white solid.

$^1$H NMR (400 MHz, d6-DMSO): δ 8.56 (1H, d, J=2.0 Hz), 8.39 (1H, d, J=2.0 Hz), 8.14 (2H, d, J=8.8 Hz), 8.01-7.94 (2H, m), 7.87 (1H, t, J=7.8 Hz), 7.83-7.76 (2H, m), 7.69 (2H, d, J=8.8 Hz), 7.61-7.57 (2H, m), 7.34-7.26 (3H, m), 4.08-3.98 (4H, m), 3.37 (3H, s), 1.87-1.74 (2H, m), 1.64-1.48 (4H, m), 1.41-1.22 (2H, m).

LCMS (Method 3): Rt=3.61 min, m/z 535.3 [M]+

Example 8. 1-(4-cyano-phenyl)-5-[4-cyclopentylcarbamoyl-2-methyl-5-oxo-1-(3-trifluoromethyl-phenyl)-2,5-dihydro-1H-pyrazol-3-yl]-4-methyl-1H-[1,2,4]triazol-4-ium benzenesulfonate

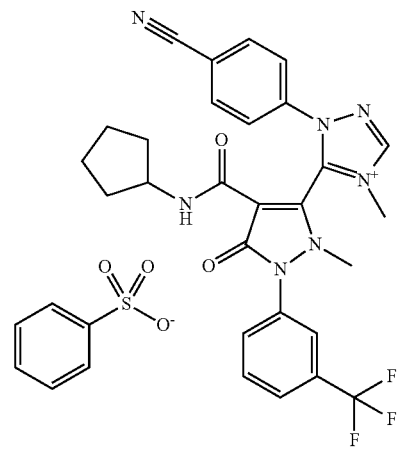 [SMILES: O=S(=O)([O-])c1ccccc1 ; Cn1c(-c2n(-c3ccc(C#N)cc3)nc[n+]2C)c(C(=O)NC2CCCC2)c(=O)n1-c1cccc(C(F)(F)F)c1]

Intermediate 8A. 2-(4-Cyano-phenyl)-2H-[1,2,4]triazole-3-carboxylate lithium salt

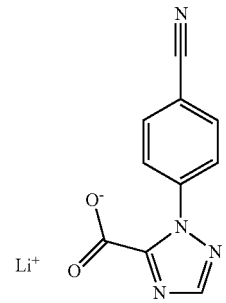 [SMILES: [Li+] ; N#Cc1ccc(-n2ncnc2C(=O)[O-])cc1]

A solution of n-butyl lithium (1.38 mL of a 1.6 M solution in hexanes, 2.2 mmol) was added dropwise to a cold (−75° C.) solution of 4-[1,2,4]triazol-1-yl-benzonitrile (340 mg, 2.0 mmol) in THF (10 ml) in an argon purged flask. The addition was at such a rate that the internal temperature did not exceed −70° C. The mixture was stirred at −75° C. for 1 h and the resultant off-white suspension was poured onto ca. 3.5 g of ground dry ice. The resultant mixture was stirred for 1 h, a thick white precipitate forming over time. The solvent was evaporated in vacuo and the residue was triturated with diethyl ether (15 mL). The solid was recovered by filtration and dried in vacuo to afford Intermediate 8A (391 mg, 1.78 mmol, 89%).

LCMS (Method U2) Rt=0.94 min, m/z 171.1 [M+H−CO2]+

Intermediate 8B.
2-(4-Cyano-phenyl)-2H-[1,2,4]triazole-3-carboxylic acid methyl ester

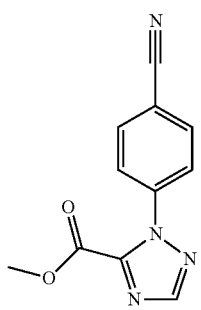 [SMILES: COC(=O)c1ncnn1-c1ccc(C#N)cc1]

Iodomethane (0.818 mL, 13.1 mmol) was added to a vigorously stirred mixture of Intermediate 8A (2.19 g, 10 mmol) and DMF (30 mL). Further aliquots of iodomethane were added after 24 h (0.325 mL, 5.3 mmol) and 48 h (0.655 mL, 10.5 mmol). The mixture was stirred for a further 3 days and the resultant solution was poured into 1:1 saturated brine:water (400 ml). The mixture was extracted with ethyl acetate (3×50 mL). The combined organic phase was washed with brine (50 mL), dried (sodium sulfate) and concentrated in vacuo to afford a yellow solid. This was purified by flash column chromatography (80 g Si column) eluting with 0-20% ethyl acetate in dichloromethane to afford Intermediate 8B as a white solid.

LCMS (Method U2) Rt=1.12 min, m/z 229.1 [M+H]+.

Intermediate 8C. 2-(4-Cyano-phenyl)-2H-[1,2,4]triazole-3-carboxylic acid N'-(3-trifluoro-methyl-phenyl)-hydrazide

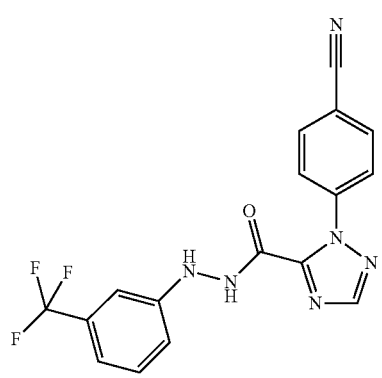 [SMILES: N#Cc1ccc(-n2ncnc2C(=O)NNc2cccc(C(F)(F)F)c2)cc1]

A mixture of 3-trifluoromethyl-phenylhydrazine hydrochloride (1.71 g, 8.03 mmol) and bis(trimethylaluminium)-1,4-diazabicyclo[2.2.2]octane adduct (2.06 g, 8.03 mmol) in dry THF (30 mL) were stirred at 40° C. for 1 h. A suspension of Intermediate 8B (1.22 g, 5.3 mmol) in dry THF (25 mL) was added and the mixture was then heated at reflux for 16 h. The cold mixture was treated by cautious dropwise addition with 4M hydrochloric acid (3.0 mL) and stirred vigorously for 5 minutes then made basic by addition of 5% aqueous potassium carbonate solution (30 mL). The mixture was diluted with water (30 mL) and extracted with ethyl acetate (3×30 mL). The combined organic phase was washed with brine (50 mL), dried (sodium sulfate) and concentrated in vacuo. The residue was purified by flash column chromatography (40 g Si column eluted with 0-25% ethyl acetate in DCM) to afford Intermediate 8C (1.48 g, 3.98 mmol) as a cream solid.

LCMS (Method U2) Rt=1.39 min, m/z 373.1 [M+H]+.

Intermediate 8D. Bis-BOC-protected-2-(4-Cyano-phenyl)-2H-[1,2,4]triazole-3-carboxylic acid N'-(3-trifluoromethyl-phenyl)-hydrazide

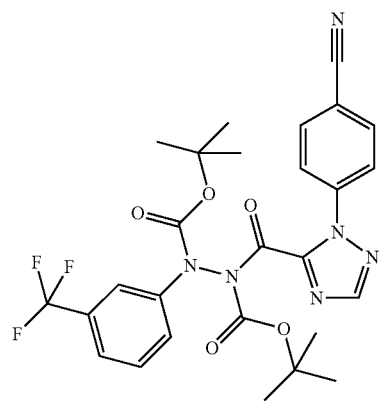 [SMILES: CC(C)(C)OC(=O)N(C(=O)c1ncnn1-c1ccc(C#N)cc1)N(C(=O)OC(C)(C)C)c1cccc(C(F)(F)F)c1]

4-Dimethylamino pyridine (24.5 mg, 0.2 mmol) was added to a mixture of Intermediate 8C (1.48 g, 3.98 mmol), di-tert-butyl dicarbonate (1.91 g, 8.75 mmol), triethylamine (1.39 ml, 9.95 mmol) and dry THF (30 mL). The mixture was heated at 50° C. for 16 h. The mixture was concentrated in vacuo. The residue was taken into ethyl acetate (30 mL) and washed with 5% potassium hydrogen sulphate solution (2×25 mL) and brine (25 mL). The solution was dried (sodium sulfate) and concentrated in vacuo to afford Intermediate 8D (2.27 g, 3.96 mmol) as a white foam.

LCMS (Method U2) Rt=1.76 min, m/z 573.2 [M+H]+.

Intermediate 8E. N'-[2-(4-Cyano-phenyl)-2H-[1,2,4]triazole-3-carbonyl]-N-(3-trifluoromethyl-phenyl)-hydrazinecarboxylic acid tert-butyl ester

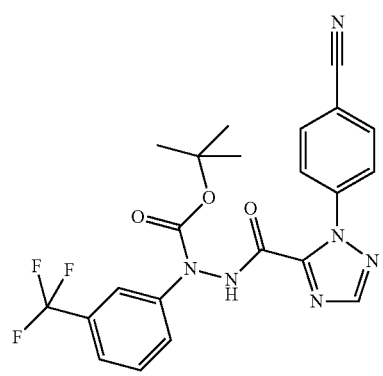 [SMILES: CC(C)(C)OC(=O)N(NC(=O)c1ncnn1-c1ccc(C#N)cc1)c1cccc(C(F)(F)F)c1]

Magnesium perchlorate (177 mg, 0.79 mmol) was added to a solution of Intermediate 8D (2.27 g, 3.96 mmol) in dry acetonitrile (60 mL). The mixture was stirred and heated at 50° C. for 2 h. A second aliquot of magnesium perchlorate (177 mg, 0.79 mmol) was added and heating was continued for a further 2 h. The cold mixture was concentrated to a small volume and diluted with saturated aqueous sodium hydrogen carbonate solution (25 mL). The mixture was extracted with ethyl acetate (3×25 mL). The combined organic phase was dried (sodium sulfate) and concentrated in vacuo. The residue was purified by flash column chromatography (40 g Si column eluted with 0-10% ethyl acetate in dichloromethane) to afford Intermediate 8E (1.21 g, 2.56 mmol) as a white foam.

LCMS (Method U2) Rt=1.56 min, m/z 471.1 [M–H]—.

Intermediate 8F. N'-[2-(4-Cyano-phenyl)-2H-[1,2,4]triazole-3-carbonyl]-N'-methyl-N-(3-trifluoromethyl-phenyl)-hydrazinecarboxylic acid tert-butyl ester

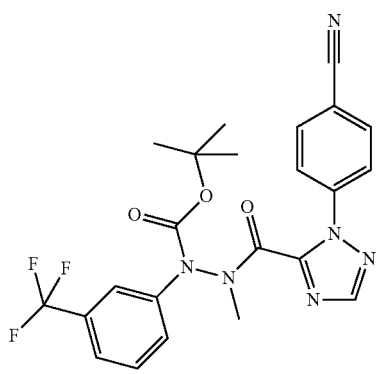 [SMILES: CN(C(=O)c1ncnn1-c1ccc(C#N)cc1)N(C(=O)OC(C)(C)C)c1cccc(C(F)(F)F)c1]

Sodium hydride (133 mg of a 60% dispersion in mineral oil, 3.33 mmol) was added to a solution of Intermediate 8E (1.21 g, 2.56 mmol) in dry DMF (25 mL). The mixture was stirred for 1 h then treated with iodomethane (175 μL, 2.82 mmol). The mixture was stirred for 2 h then diluted with brine:water 2:1 (200 mL). The mixture was extracted with ethyl acetate (3×25 mL). The combined organic phase was dried (sodium sulfate) and concentrated in vacuo. The residue was purified by flash column chromatography (40 g Si cartridge eluted with 0-10% ethyl acetate in DCM) to afford Intermediate 8F (1.06 g, 2.18 mmol) as a white foam.

LCMS (Method U2) Rt=1.64 and 1.66 min, m/z 431.1 [M+H–C$_4$H$_9$]+.

Intermediate 8G. 2-(4-Cyano-phenyl)-2H-[1,2,4]triazole-3-carboxylic acid N-methyl-N'-(3-trifluoromethyl-phenyl)-hydrazide

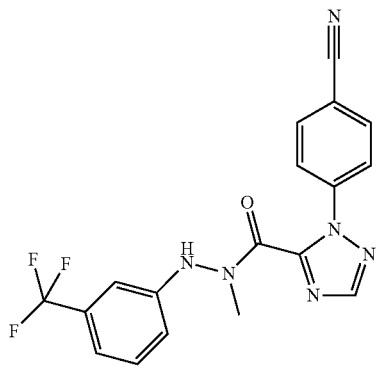 [SMILES: CN(Nc1cccc(C(F)(F)F)c1)C(=O)c1ncnn1-c1ccc(C#N)cc1]

A mixture of Intermediate 8F (950 mg, 1.95 mmol), trifluoroacetic acid (2.5 mL), dichloromethane (2.5 mL) and trisopropyl silane (0.25 mL) was stirred for 1 h at ambient temperature then concentrated in vacuo to afford a syrup. This was twice concentrated from toluene to afford a yellow solid that was purified by flash column chromatography (40 g Si column eluted with 0-4% 2M methanolic ammonia in dichloromethane). This gave Intermediate 8G (734 mg, 1.90 mmol).

LCMS (Method U2) Rt=1.37 min, m/z 387.1 [M+H]+.

Intermediate 8H. 3-[N'-[2-(4-Cyano-phenyl)-2H-[1,2,4]triazole-3-carbonyl]-N'-methyl-N-(3-trifluoromethyl-phenyl)-hydrazino]-3-oxo-propionic acid ethyl ester

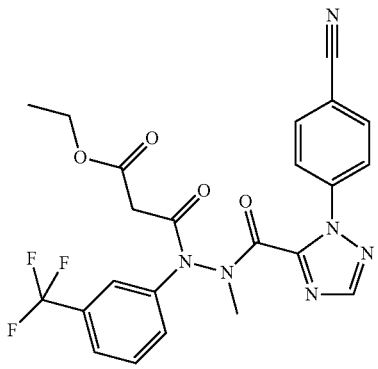 [SMILES: CCOC(=O)CC(=O)N(c1cccc(C(F)(F)F)c1)N(C)C(=O)c1ncnn1-c1ccc(C#N)cc1]

A mixture of Intermediate 8G (734 mg, 1.90 mmol), ethyl malonyl chloride (0.268 mL, 2.09 mmol), pyridine (0.185 mL, 2.28 mmol), 4-dimethylamino-pyridine (2.5 mg, 0.02 mmol) and dry tetrahydrofuran (20 mL) was stirred at 50° C. Further aliquots of ethyl malonyl chloride (0.268 mL, 2.09 mmol) and pyridine (0.185 mL, 2.28 mmol) were added after 16 h and again after 23 h reaction time. Heating was discontinued after 39 h. The mixture was concentrated in vacuo. The residue was taken into ethyl acetate (30 mL) and washed with water (25 mL) and brine (25 mL) then dried (sodium sulfate) and concentrated in vacuo. The residue was purified by flash column chromatography (40 g Si cartridge eluted with 0-15% ethyl acetate in DCM) to afford Intermediate 8H (0.86 g, 1.71 mmol) as a white foam.

LCMS (Method U2) Rt=1.46 min, m/z 501.1 [M+H]+.

Intermediate 8I. 5-[2-(4-Cyano-phenyl)-2H-[1,2,4]triazol-3-yl]-1-methyl-3-oxo-2-(3-trifluoro-methyl-phenyl)-2,3-dihydro-1H-pyrazole-4-carboxylic acid ethyl ester

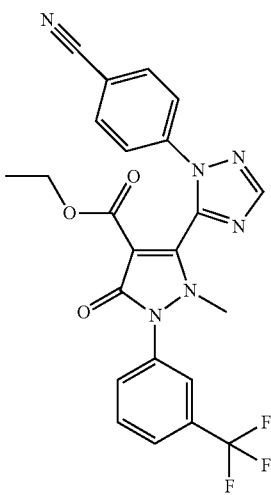 [SMILES: CCOC(=O)c1c(-c2ncnn2-c2ccc(C#N)cc2)n(C)n(-c2cccc(C(F)(F)F)c2)c1=O]

Sodium ethoxide (234 mg, 3.44 mmol) was added to a stirred suspension of Intermediate 8H (0.86 g, 1.71 mmol) in absolute ethanol (15 mL). The mixture was stirred at 40° C. for 18 h giving a thick suspension. The cold mixture was treated with 10% aqueous citric acid (20 mL) and extracted with ethyl acetate (2×20 mL). The combined organic phase was dried (sodium sulfate) and concentrated in vacuo. The residue was purified by flash column chromatography (40 g Si cartridge eluted with 0-10% ethyl acetate in dichloromethane) to afford Intermediate 8I (720 mg, 1.49 mmol) as a white foam.

LCMS (Method U2) Rt=1.28 min, m/z 483.1 [M+H]+.

Intermediate 8J. 5-[2-(4-Cyano-phenyl)-2H-[1,2,4]triazol-3-yl]-1-methyl-3-oxo-2-(3-trifluoro-methyl-phenyl)-2,3-dihydro-1H-pyrazole-4-carboxylic acid

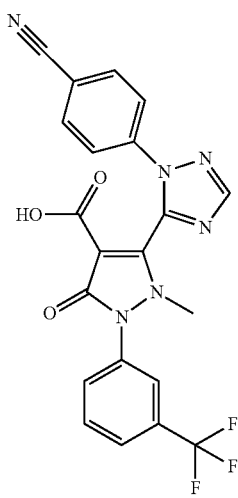 [SMILES: Cn1c(-c2ncnn2-c2ccc(C#N)cc2)c(C(=O)O)c(=O)n1-c1cccc(C(F)(F)F)c1]

A solution of lithium hydroxide hydrate (313 mg, 7.45 mmol) in water (5 mL) was added to a solution of Intermediate 8I (720 mg, 1.49 mmol) in tetrahydrofuran (15 mL). The mixture was stirred at RT for 5 h. The mixture was then treated with 5% aqueous potassium hydrogen sulfate solution (20 mL) and extracted with ethyl acetate (2×15 mL). The combined organic phase was washed with brine, dried (sodium sulfate) and concentrated in vacuo to afford Intermediate 8J (556 mg, 1.22 mmol) as a white solid.

LCMS (Method U2) Rt=1.29 min, m/z 455.1 [M+H]+.

Intermediate 8K. 5-[2-(4-Cyano-phenyl)-2H-[1,2,4]triazol-3-yl]-1-methyl-3-oxo-2-(3-trifluoromethyl-phenyl)-2,3-dihydro-1H-pyrazole-4-carboxylic acid cyclopentyl-amide

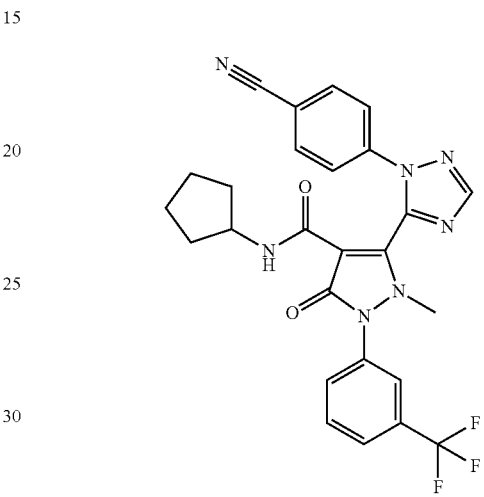

Oxalyl chloride (35 μL, 0.41 mmol) was added to a suspension of Intermediate 8J (114 mg, 0.25 mmol) in dry dichloromethane (2.0 mL). The mixture was stirred at RT for 3 h then dimethyl formamide (5 μL) was added. The mixture was stirred for a further 30 minutes then concentrated to dryness in vacuo. The residue was suspended in dry dichloromethane (3.0 mL) and cyclopentyl amine (49 μL, 0.5 mmol) was added followed by DIPEA (88 μL, 0.5 mmol). The mixture was stirred for 1 h. The resultant solution was filtered through a 2 g flash NH2 cartridge washing with dichloromethane and ethyl acetate. Concentration of the combined filtrate gave the crude product. This was further purified by flash column chromatography (2 g Si-II column eluted with 0-50% ethyl acetate in dichloromethane) and trituration with ethyl acetate to afford Intermediate 8K (55 mg, 0.105 mmol) as a white solid.

LCMS (Method U2) Rt=1.44 min, m/z 522.2 [M+H]+.

1-(4-cyano-phenyl)-5-[4-cyclopentylcarbamoyl-2-methyl-5-oxo-1-(3-trifluoromethyl-phenyl)-2,5-dihydro-1H-pyrazol-3-yl]-4-methyl-1H-[1,2,4]triazol-4-ium benzenesulfonate Methyl benzenesulfonate (20 μL, 0.15 mmol) was added to a solution of Intermediate 8K (55 mg, 0.105 mmol) in dichloromethane (2.0 mL). The mixture was concentrated under a stream of nitrogen until solid began to appear. The mixture was heated at 41° C. for 3.5 h but reaction was sluggish. A second aliquot of methyl benzenesulfonate (100 μL, 0.75 mmol) was added and heating was continued for 16 h. Most of the solvent was lost. Acetonitrile (0.25 mL) was added and heating was increased to 60° C. After 24 h a further aliquot each of acetonitrile (0.25 mL) and methyl benzenesulfonate (100 μL, 0.75 mmol) were added and heating was increased to 70° C. After a further 24 h the mixture was cooled to afford the crude product. This was purified by flash column chromatography (1 g Si column eluted with 2%, 10% then 20% methanol in dichloromethane). The product thus obtained was freeze-dried from acetonitrile/water to afford the title compound (54 mg, 0.073 mmol) as a white solid.

¹H NMR (400 MHz, d6-DMSO): δ 9.90 (1H, s), 8.16 (2H, d J=8.8 Hz), 8.03-7.86 (5H, m), 7.82 (2H, d, J=8.8 Hz), 7.62 (2H, m), 7.34-7.26 (3H, m), 4.10 (3H, s), 4.04-3.94 (1H, m), 3.48 (3H, s), 1.84-1.70 (2H, m), 1.62-1.48 (3.5H*, m), 1.40-1.30 (1H, m), 1.30-1.20 (1.5H*, m). *Indicates signals exhibiting rotameric effects.

LCMS (Method 3): Rt=3.65 min, m/z 536.3 [M]+

Example 9. [2-(5-Cyano-2-{5-[3-cyclopentylcarbamoyl-5-methyl-2-oxo-1-(3-trifluoromethyl-phenyl)-2,3-dihydro-H-imidazol-4-yl]-pyrazol-1-yl}-phenyl)-ethyl]-trimethyl-ammonium benzene sulfonate

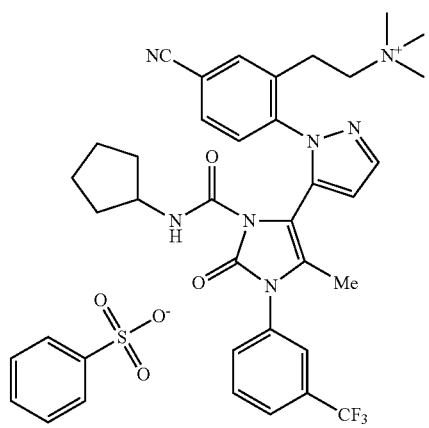 [SMILES: O=S(=O)([O-])c1ccccc1 ; Cc1c(-c2ccnn2-c2ccc(C#N)cc2CC[N+](C)(C)C)n(C(=O)NC2CCCC2)c(=O)n1-c1cccc(C(F)(F)F)c1]

Intermediate 9A. 1-[2-Ethoxy-5-methyl-1-(3-trifluoromethyl-phenyl)-1H-imidazol-4-yl]-ethanone

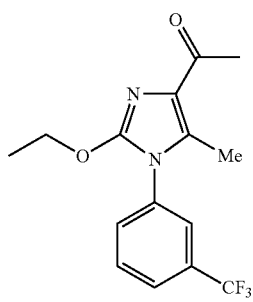 [SMILES: CCOc1nc(C(C)=O)c(C)n1-c1cccc(C(F)(F)F)c1]

4-Bromo-2-ethoxy-5-methyl-1-[3-(trifluoromethyl)phenyl]-1H-imidazole (Intermediate 1D, 700 mg, 2 mmol), tributyl(1-ethoxyvinyl)tin (940 mg, 2.6 mmol), bis(triphenylphosphine)palladium(II) dichloride (70 mg, 0.1 mmol), DMF (7 ml) and 1 M HCl (14 ml) were mixed in each of 3 sealed, degassed (N₂) vials which were heated at 120° C. for 1.5 h. The reaction mixtures were combined and treated with 1M HCl (50 ml) and stirred vigorously for 30 min. Water and EtOAc were added and the separated organic phase was washed with water (×2) brine, dried (Na₂SO₄) filtered and evaporated to give a brown oil which was purified by chromatography using 10% to 40% EtOAc in cyclohexane to give Intermediate 9A as a yellow oil which crystallised upon cooling (0.91 g, 34%).

LCMS (Method 2) Rt=3.20 min., m/z 285.2 [M+H]+

Intermediate 9B. 3-Dimethylamino-1-[2-ethoxy-5-methyl-1-(3-trifluoromethyl-phenyl)-1H-imidazol-4-yl]-propenone

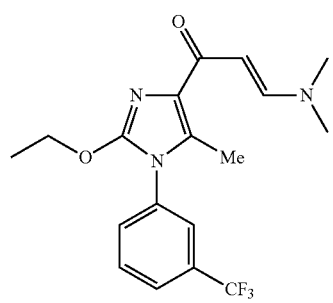 [SMILES: CCOc1nc(C(=O)/C=C/N(C)C)c(C)n1-c1cccc(C(F)(F)F)c1]

1-[2-Ethoxy-5-methyl-1-(3-trifluoromethyl-phenyl)-1H-imidazol-4-yl]-ethanone (Intermediate 9A, 1.68 g, 5.38 mmol) and Bredereck's reagent (8 ml) were mixed and heated at 100° C. for a total of 3 h then allowed to stand for 2 days. The Bredereck's reagent was partially evaporated in vacuo at 50° C. and the concentrate was diluted with EtOAc, washed with water (×3), brine, dried (Na₂SO₄) and evaporated to give Intermediate 9B as an orange gum which crystallised on standing (1.8 g, 91%).

LCMS (Method 2) Rt=2.85 min., m/z 368.3 [M+H]+

Intermediate 9C. 3-((E)-2-dimethylamino-vinyl)-4 nitro-benzonitrile

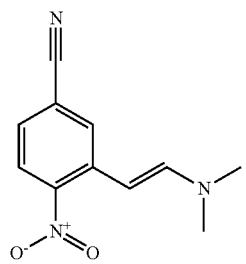 [SMILES: CN(C)/C=C/c1cc(C#N)ccc1[N+](=O)[O-]]

A mixture of 3-methyl-4-nitrobenzonitrile (486 mg, 3 mmol) and N,N-dimethylformamide dimethyl acetal (6 mL) was heated at 100° C. under an inert atmosphere for 2 days (reaction progress was monitored by ¹H NMR of aliquots concentrated in vacuo). The cold mixture was concentrated in vacuo to leave a dark solid. The residue was taken into dichloromethane and filtered through a short pad of silica. The filtrate was concentrated in vacuo to afford Intermediate 9C (495 mg, 2.28 mmol, 76%).

¹H NMR (400 MHz, CDCl₃): δ 7.84 (1H, d J=8.4 Hz), 7.72 (1H, d J=1.6 Hz), 7.14 (1H, dd J=8.4 and 1.6 Hz), 7.02 (1H, d J=13.4 Hz), 5.74 (1H, d J=13.4), 2.97 (6H, s).

Intermediate 9D.
3-(2-Dimethylamino-ethyl)-4-nitro-benzonitrile

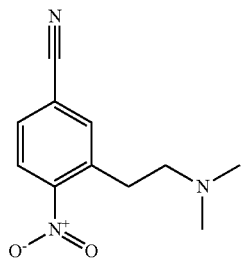 [SMILES: CN(C)CCc1cc(C#N)ccc1[N+](=O)[O-]]

A solution of Intermediate 9C (495 mg, 2.28 mmol) in dichloromethane (15 mL) was treated with sodium triacetoxyborohydride (2.12 g, 10 mmol). The reaction mixture was stirred at ambient temperature for 4 h, the mixture fading from near black to pale red/brown. Water (20 mL) was added and stirring was continued for 10 min. whilst the mixture degassed. The mixture was diluted with sufficient saturated sodium carbonate solution to make the aqueous phase basic and the phases were separated. The aqueous phase was extracted with further dichloromethane (3×10 mL). The combined organic phase was dried (sodium sulfate) and loaded onto a 5 g SCX-2 cartridge. This was rinsed with 4:1 dichloromethane: methanol then the basic material was eluted with 4:1 dichloromethane: 2M methanolic ammonia. Concentration of the appropriate fractions gave Intermediate 9D (395 mg, 1.8 mmol, 79%) as a fawn solid.

LCMS (Method U2) Rt=0.30 min, m/z 220.1 [M+H]+

Intermediate 9E.
4-Amino-3-(2-dimethylamino-ethyl)-benzonitrile

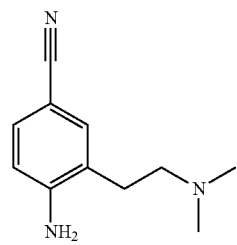

A mixture of Intermediate 9D (395 mg, 1.8 mmol), powdered iron (605 mg, 10.8 mmol) ammonium chloride (867 mg, 16.2 mmol) and 1:1 methanol: water (16 mL) was stirred and heated at 80° C. for 1 h. The mixture was cooled and filtered through a pad of celite washing with water and a little methanol. The filtrate was made basic with saturated sodium carbonate solution and extracted with EtOAc (3×25 mL) then dichloromethane (25 mL). The combined organic phase was dried (sodium sulfate) and concentrated in vacuo to afford Intermediate 9E (325 mg, 1.7 mmol, 94%) as a brown oil that became solid on standing.

LCMS (Method U2) Rt=0.24 min, m/z 190.2 [M+H]+

Intermediate 9F.
3-(2-Dimethylamino-ethyl)-4-hydrazino-benzonitrile

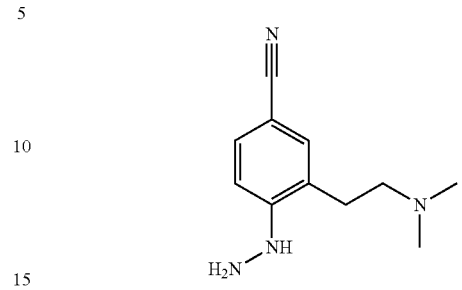

A solution of sodium nitrite (117 mg, 1.7 mmol) in water (0.7 mL) was added dropwise over 5 min. to a cold (approx. −10° C.) solution of Intermediate 9E (320 mg, 1.7 mmol) in concentrated hydrochloric acid (3.4 mL). The mixture was stirred cold for 15 min. Then a solution of tin(II)chloride dihydrate (840 mg, 3.73 mmol) in concentrated hydrochloric acid (1 mL) was added dropwise over 5 minutes. The mixture was stirred cold for 1 h then made slightly basic by cautious addition of 5M sodium hydroxide solution. The white suspension was extracted with dichloromethane (4×10 mL). The combined organic phase was dried (sodium sulfate) and concentrated in vacuo to afford crude Intermediate 9F as a brown oil (210 mg). This was used crude in the next step.

LCMS (Method U2) Rt=0.14 min, m/z 205.1 [M+H]+

Intermediate 9G. 3-(2-Dimethylamino-ethyl)-4-{5-[5-methyl-2-oxo-1-(3-trifluoromethyl-phenyl)-2,3-dihydro-1H-imidazol-4-yl]-pyrazol-1-yl}-benzonitrile

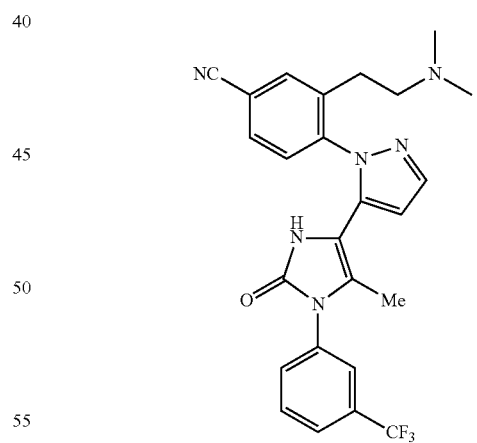

Concentrated hydrochloric acid (0.25 mL, ca. 3 mmol) was added to a solution of Intermediate 9B (224 mg, 0.61 mmol) in isopropyl alcohol (6 mL). The resultant solution was immediately mixed with crude Intermediate 9F (200 mg, ca. 0.7 mmol) and the mixture heated at 85° C. for 1.5 h then cooled to ambient temperature. The cold reaction mixture was loaded onto a 5 g flash SCX-2 column. The column was washed with 4:1 dichloromethane: methanol then the basic fraction was eluted with 4:1 dichloromethane: 2M methanolic ammonia. The basic fraction was concentrated in vacuo to afford the crude product. This was further purified by flash chromatography on a 5 g flash Si II column eluting with 50:1, 25:1 then 25:2 dichloromethane: methanol. Concentration of the appropriate fractions gave Intermediate 9G (225 mg, 0.46 mmol, 75%).

LCMS (Method U2) Rt=0.98 min, m/z 481.2 [M+H]+

Intermediate 9H. 5-{2-[4-Cyano-2-(2-dimethyl-amino-ethyl)-phenyl]-2H-pyrazol-3-yl}-4-methyl-2-oxo-3-(3-trifluoromethyl-phenyl)-2,3-dihydro-imidazole-1-carboxylic acid cyclopentylamide

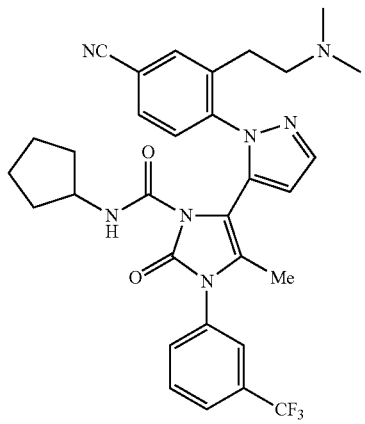 [SMILES: Cc1c(-c2ccnn2-c2ccc(C#N)cc2CCN(C)C)n(C(=O)NC2CCCC2)c(=O)n1-c1cccc(C(F)(F)F)c1]

A mixture of Intermediate 9G (220 mg, 0.45 mmol), cyclopentyl isocyanate (150 mg, 152 μL, 1.35 mmol) and ethyldiisopropylamine (175 mg, 235 μL, 1.35 mmol) in dichloromethane (5.0 mL) was heated, under an inert atmosphere, at 43° C. for 25 h. The cold mixture was concentrated in vacuo and the residue was purified by chromatography on a 5 g Si II column eluting with dichloromethane, 25:1 then 25:2 dichloromethane: methanol. The product thus obtained was further purified using a 2 g flash SCX-2 column onto which it was loaded in dichloromethane. The column was washed with 4:1 dichloromethane: methanol then the basic fraction was eluted with 4:1 dichloromethane: 2M methanolic ammonia. The basic fraction was concentrated in vacuo to afford the crude product. This was triturated with ether and dried in vacuo to afford Intermediate 9H (110 mg, 0.18 mmol, 40%).

LCMS (Method U2) Rt=1.19 min, m/z 592.3 [M+H]+

[2-(5-Cyano-2-{5-[3-cyclopentylcarbamoyl-5-methyl-2-oxo-1-(3-trifluoromethyl-phenyl)-2,3-dihydro-1H-imidazol-4-yl]-pyrazol-1-yl}-phenyl)-ethyl]-trimethyl-ammonium benzene sulfonate Methyl benzenesulfonate (17 mg, 14 μL, 0.1 mmol) was added to a solution of afford Intermediate 9H (50 mg, 0.084 mmol) in dichloromethane (0.5 mL). The mixture was stirred for 18 h, ethyldiisopropylamine (5 μL, 0.028 mmol) and methyl benzenesulfonate (5 μL, 0.04 mmol) were added and the mix was stirred for a further 4 h. The mixture was diluted with dichloromethane and loaded onto a 2 g flash NH2 cartridge. This was eluted with 10:1 dichloromethane: methanol. Concentration of the appropriate fractions in vacuo gave the crude product. This was further purified on a 2 g C18 reverse phase cartridge (pre-equilibrated at 10% acetonitrile in water) eluting with 15, 20, 25, 30, 40 then 50% acetonitrile in water. Monitoring by LCMS allowed identification of the product fraction which was freeze-dried to afford the title compound (49 mg, 0.064 mmol, 76%).

LCMS (Method 3): Rt=4.15 min, m/z 606.4 [M]+

$^1$H NMR (400 MHz, CDCl$_3$): δ 8.37 (1H, d J=7.1 Hz), 8.15 (1H, d J=1.8 Hz), 7.98-7.93 (2H, m), 7.77-7.73 (2H, m), 7.67 (1H, t J=7.9 Hz), 7.59-7.54 (2H, m), 7.49 (1H, d J=7.9 Hz), 7.42-7.32 (3H, m), 7.13 (1H, d J=8.3 Hz), 6.57 (1H, d J=1.8 Hz), 4.18-4.08 (1H, m), 3.98-3.82 (2H, m), 3.41 (9H, s), 3.25-3.12 (2H, m), 1.94 (3H, s), 1.88-1.76 (2H, m), 1.63-1.50 (4H, m), 1.43-1.34 (1H, m) 1.28-1.19 (1H, m).

The following compounds were prepared by analogous procedures to that used in Example 9 using the suitable isocyanate for compounds 11-14 and the suitable alkylating agent for compound 10.

| Ex | Structure | 1H NMR | LC-MS Method 3 |
|---|---|---|---|
| 10 | (structure shown: compound with NC, benzyl-N+(Me)(Me), pyrazole, cyclopentyl carbamoyl imidazolone, 3-CF3-phenyl, Br⁻ counterion) | 1H NMR [400 MHz, CDCl3] 8.42 (1H, d, J = 7.1 Hz), 8.17 (1H, d, J = 1.8 Hz), 7.77-7.72 (1H, m), 7.72-7.64 (4H, m), 7.63-7.57 (2H, m), 7.55-7.44 (4H, m), 7.19 (1H, d, J = 8.3 Hz), 6.57 (1H, d, J = 1.8 Hz), 5.08 (1H, d, J = 12.6 Hz), 4.96 (1H, d, J = 12.6 Hz), 4.42 (1H, td, J = 11.8, 6.2 Hz), 4.03 (1H, td, J = 12.2, 4.6 Hz), 3.91-3.82 (1H, m), 3.38-3.21 (7H, m), 1.97 (3H, s), 1.89-1.75 (2H, m), 1.67-1.50 (5H, m), 1.45-1.33 (1H, m), 1.30-1.19 (1H, m) | LCMS Rt = 4.44, m/z = 682 |

| Ex | Structure | 1H NMR | LC-MS Method 3 |
|---|---|---|---|
| 11 | 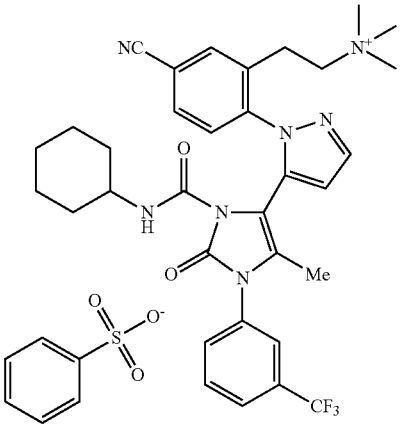 [SMILES: O=S(=O)([O-])c1ccccc1 ; Cc1c(-c2ccnn2-c2ccc(C#N)cc2CC[N+](C)(C)C)n(C(=O)NC2CCCCC2)c(=O)n1-c1cccc(C(F)(F)F)c1] | 1H NMR [400 MHz, CDCl3] 8.95-8.86 (1H, m), 8.43 (1H, d, J = 7.8 Hz), 8.13 (1H, s), 7.99-7.95 (2H, m), 7.79-7.72 (2H, m), 7.69 (1H, t, J = 8.0 Hz), 7.62-7.55 (2, m), 7.53-7.47 (1H, m), 7.42-7.38 (1H, m), 7.14 (2H, d, J = 8.7 Hz), 6.58 (1H, d, J = 1.8 Hz), 4.27-4.13 (1H, m), 4.03-3.90 (1H, m), 3.51-3.32 (10H, m), 3.26-3.13 (2H, m), 1.96 (3H, s), 1.93-1.71 (3H, m), 1.71-1.42 (2H, m), 1.42-1.06 (5H, m) | LCMS Rt = 4.23, m/z = 620 |
| 12 | 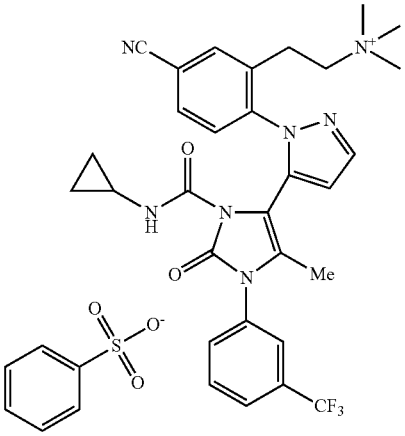 [SMILES: O=S(=O)([O-])c1ccccc1 ; Cc1c(-c2ccnn2-c2ccc(C#N)cc2CC[N+](C)(C)C)n(C(=O)NC2CC2)c(=O)n1-c1cccc(C(F)(F)F)c1] | 1H NMR [400 MHz, CDCl3] 8.45 (1H, d, J = 3.3 Hz), 8.18 (1H, d, J = 1.6 Hz), 7.99-7.92 (2H, m), 7.78-7.71 (2H, m), 7.67 (1H, t, J = 7.8 Hz), 7.59-7.52 (2H, m), 7.49-7.44 (1H, m), 7.43-7.32 (3H, m), 7.12 (1H, d, J = 8.3 Hz), 6.58 (1H, d, J = 2.1 Hz), 4.18-4.06 (1H, m), 4.01-3.89 (1H, m), 3.41 (9H, s), 3.30-3.19 (2H, m), 2.54-2.46 (1H, m), 1.93 (3H, s), 0.75-0.63 (2H, m), 0.51-0.41 (1H, m), 0.35-0.28 (1H, m) | LCMS Rt = 3.85, m/z = 578 |
| 13 | 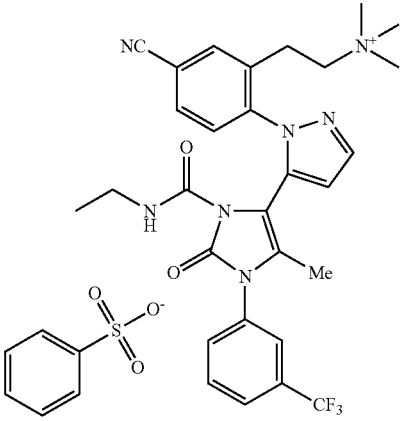 [SMILES: O=S(=O)([O-])c1ccccc1 ; CCNC(=O)n1c(-c2ccnn2-c2ccc(C#N)cc2CC[N+](C)(C)C)c(C)n(-c2cccc(C(F)(F)F)c2)c1=O] | 1H NMR [400 MHz, DMSO-d6] 8.20 (1H, t, J = 11.3 Hz), 8.09 (1H, d, J = 1.7 Hz), 7.95-7.913 (1H, m), 7.91-7.86 (2H, m), 7.86-7.77 (3H, m), 7.62-7.57 (2H, m), 7.40 (1H, d, J = 8.3 Hz), 7.34-7.26 (3H, m), 6.68 (1H, d, J = 1.7 Hz), 3.85-3.53 (2H, m), 3.12 (9H, s), 3.05-2.96 (4H, m), 1.92 (3H, s), 0.90 (3H, t, J = 7.3 Hz) | LCMS Rt = 3.73, m/z = 566 |

| Ex | Structure | 1H NMR | LC-MS Method 3 |
|---|---|---|---|
| 14 | 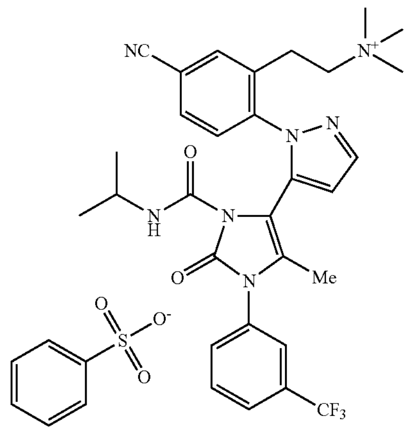 [SMILES: O=S(=O)([O-])c1ccccc1 ; Cc1c(-c2ccnn2-c2ccc(C#N)cc2CC[N+](C)(C)C)n(C(=O)NC(C)C)c(=O)n1-c1cccc(C(F)(F)F)c1] | 1H NMR [400 MHz, CDCl$_3$] 8.27 (1H, 7.4 Hz), 8.18 (1H, d, J = 1.6 Hz), 8.00-7.94 (2H, m), 7.78-7.72 (2H, m), 7.68 (1H, t, J = 7.9 Hz), 7.61-7.53 (2H, m), 7.52-7.46 (1H, m), 7.43-7.32 (3H, m), 7.12 (1H, d, J = 8.3 Hz), 6.58 (1H, d, J = 1.8 Hz), 4.25-4.13 (1H, m), 3.99-3.87 (1H, m), 3.76-3.64 (1H, m), 3.42 (9H, s), 3.26-3.15 (2H, m), 1.96 (3H, s), 1.10 (3H, d, J = 6.4 Hz), 1.03 (3H, d, J = 6.4 Hz) | LCMS Rt = 4.42, m/z = 580 |

Example 15. (2-{5-Cyano-2-[4'-cyclopentylcarbamoyl-2'-methyl-5'-oxo-1'-(3-trifluoromethyl-phenyl)-2',5'-dihydro-1'H-[3,3']bipyrazolyl-2-yl]-phenyl}-ethyl)-trimethyl-ammonium benzene sulfonate

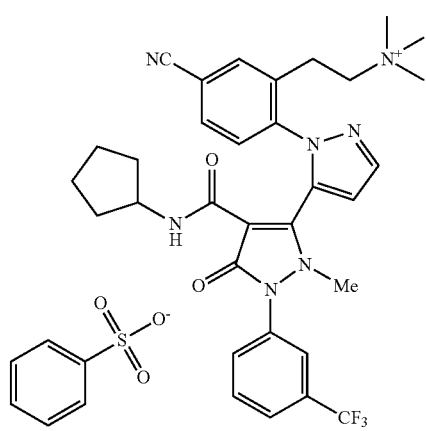 [SMILES: O=S(=O)([O-])c1ccccc1 ; Cn1c(-c2ccnn2-c2ccc(C#N)cc2CC[N+](C)(C)C)c(C(=O)NC2CCCC2)c(=O)n1-c1cccc(C(F)(F)F)c1]

Intermediate 15A. Propionic acid N'-(3-trifluoromethyl-phenyl)-hydrazide

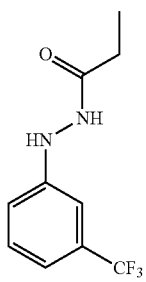

A suspension of 3-(trifluoromethyl)-phenylhydrazine hydrochloride (9.6 g, 45.2 mmol) was formed in DCM (300 mL) at room temperature. Triethylamine (4.08 mL, 100 mmol) was added followed by the dropwise addition of propionyl chloride (13.9 mL, 46.7 mmol). The mixture was stirred for 2 h at room temperature. The mixture was washed with aqueous sodium carbonate (100 mL, 50% saturated) and brine (100 mL) then dried (Na$_2$SO$_4$), filtered and evaporated. The residue was recrystallized from a 1:1 mixture of cyclohexane:ethyl acetate giving a first crop of Intermediate 15A as a white solid (3.09 g). The filtrate was concentrated dissolved in a mixture of ethyl acetate, cyclohexane and DCM then purified by flash chromatography on a 340 g Biotage column eluting with a gradient of 20%-80% ethyl acetate in cyclohexane. Concentration of the appropriate fractions gave further Intermediate 15A (5.22 g, 88% yield in total).

LCMS (Method U2) Rt=1.09 min, m/z 233 [M+H]+

Intermediate 15B. N'-Propionyl-N-(3-trifluoromethyl-phenyl)-hydrazinecarboxylic acid benzyl ester

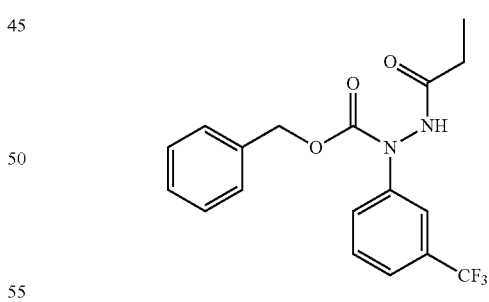

A mixture of Intermediate 15A (8 g, 34.5 mmol) and triethylamine (12 mL, 86.2 mmol) was formed in THF (230 mL). Benzyl chloroformate (5.91 mL, 41.4 mmol) was added dropwise and the mixture stirred at room temperature for 4 h. Further benzyl chloroformate (3.0 mL, 20.7 mmol) was added and the mixture stirred over night at room temperature. Another portion of benzyl chloroformate (5.91 mL, 41.4 mmol) was added followed by a second after an additional 4 h. The mixture was allowed to stand at room temperature overnight. The solvent was removed and the residue was partitioned between ethyl acetate and water, washed with saturated aqueous sodium carbonate, 10% citric acid solution then dried (Na$_2$SO$_4$), filtered and evaporated. The residue was purified by flash chromatography on a 340 g Biotage column eluting with a gradient of 15%-40% ethyl acetate in cyclohexane. Concentration of the appropriate fractions gave Intermediate 15B as a colourless oil which gradually solidified to a white solid (6.3 g, 50% yield).

LCMS (Method U2) Rt=1.52 min, m/z 389 [M+Na]+

Intermediate 15C. N'-Methyl-N'-propionyl-N-(3-trifluoromethyl-phenyl)-hydrazinecarboxylic acid benzyl ester

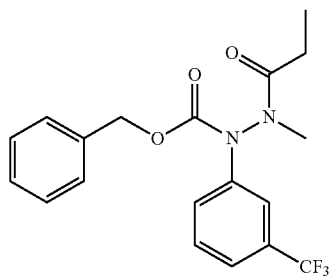 [SMILES: CCC(=O)NN(C(=O)OCc1ccccc1)c1cccc(C(F)(F)F)c1]

A solution of Intermediate 15B (6.2 g, 16.9 mmol) was formed in dry DMF. Sodium hydride (745 mg, 60% suspension in mineral oil, 18.63 mmol) was added portionwise. After complete addition the mixture was stirred for 35 minutes before iodomethane (1.21 mL, 19.5 mmol) was added. The mixture was stirred for 70 minutes at room temperature then diluted with ethyl acetate, washed with water, brine, dried (Na$_2$SO$_4$), filtered and evaporated. The residue was purified by flash chromatography on a 100 g Biotage column eluting with a gradient of 10%-40% ethyl acetate in cyclohexane. Concentration of the appropriate fractions gave Intermediate 15C as a colorless oil (5.35 g, 83% yield).

LCMS (Method U2) Rt=1.70 min, m/z 381 [M+H]+, 403 [M+Na]+

Intermediate 15D. Propionic acid N-methyl-N'-(3-trifluoromethyl-phenyl)-hydrazide

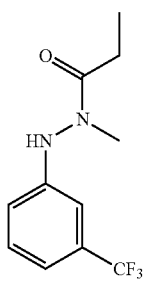

A solution of Intermediate 15C (5.3 g, 13.9 mmol) in IMS (75 mL) was added to a suspension of 10% palladium on carbon (250 mg) in IMS (25 mL). The mixture was degassed and put under an atmosphere of hydrogen gas. The mixture was stirred for 90 mins at room temperature then filtered through Celite (washing the filter with IMS). The filtrate was evaporated and the residue was purified by flash chromatography on a 50 g Biotage column eluting with a gradient of 20%-60% ethyl acetate in cyclohexane. Concentration of the appropriate fractions gave Intermediate 15D (3.14 g, 92% yield).

LCMS (Method U2) Rt=1.46 min, m/z 247 [M+H]+

Intermediate 15E. [N'-Methyl-N'-propionyl-N-(3-trifluoromethyl-phenyl)-hydrazinocarbonyl]-acetic acid ethyl ester

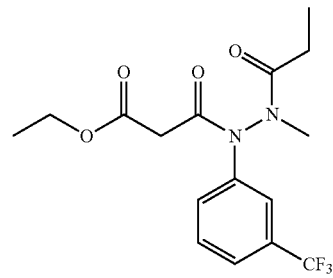 [SMILES: CCOC(=O)CC(=O)N(c1cccc(C(F)(F)F)c1)N(C)C(=O)CC]

A solution of Intermediate 15D (3.1 g, 12.6 mmol) was formed in THF (70 mL). Pyridine (1.17 mL, 14.4 mmol) and 4-dimethylaminopyridine (70 mg, cat.) were added followed by ethyl malonyl chloride (1.85 mL, 14.4 mmol). The mixture was then heated at 50° C. overnight. Further pyridine (1.17 mL, 14.4 mmol) and ethyl malonyl chloride (1.85 mL, 14.4 mmol) were added and the mixture stirred for an extra 4 h at 50° C. The solvent was evaporated and the residue partitioned between sodium bicarbonate and ethyl acetate. The organic phase was washed with water, 10% citric acid solution, brine and then dried (Na$_2$SO$_4$), filtered and evaporated. The crude mixture (5.46 g) containing two main components (Intermediate 15E and potentially malonic acid 4-ethoxycarbonyl-3-ethyl-2-methyl-5-oxo-1-(3-trifluoromethyl-phenyl)-pyrazolidin-3-yl ester ethyl ester) was carried through to the next reaction without purification.

LCMS (Method U2) Intermediate 15E: Rt=1.35 min, m/z 361 [M+H]+ and byproduct: Rt=1.51 min, m/z 497 [M+Na]+

Intermediate 15F. 5-Ethyl-1-methyl-3-oxo-2-(3-trifluoromethyl-phenyl)-2,3-dihydro-1H-pyrazole-4-carboxylic acid ethyl ester

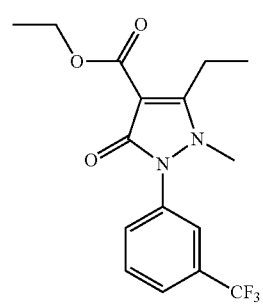 [SMILES: CCOC(=O)c1c(CC)n(C)n(-c2cccc(C(F)(F)F)c2)c1=O]

A solution of the crude mixture containing Intermediate 15E (5.25 g) was formed in absolute ethanol (75 mL). Sodium ethoxide (1.90 g, 28 mmol) was added and the mixture heated at 75° C. for 1 h. The mixture was allowed to cool then concentrated under vacuum to approximately half volume then partitioned between ethyl acetate and 10% citric acid solution. The aqueous phase was extracted with ethyl acetate and the combined organic phases were evaporated to an orange oil. The residue was purified by flash chromatography on a 100 g Biotage column eluting with a gradient of 15%-50% ethyl acetate in DCM. The appropriate fractions were concentrated then dissolved in DCM and washed with aqueous sodium carbonate, dried (Na$_2$SO$_4$), filtered and evaporated to give Intermediate 15F (1.65 g, 38% yield over two steps).

LCMS (Method U2) Rt=1.31 min, m/z 365 [M+Na]+

Intermediate 15G. (±) 5-(1-Bromo-ethyl)-1-methyl-3-oxo-2-(3-trifluoromethyl-phenyl)-2,3-dihydro-1H-pyrazole-4-carboxylic acid ethyl ester

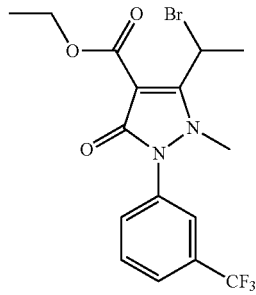 [SMILES: CCOC(=O)c1c(C(C)Br)n(C)n(-c2cccc(C(F)(F)F)c2)c1=O]

A solution of Intermediate 15F (175 mg, 0.51 mmol) was formed in chloroform (5 mL). N-bromosuccinimide (108 mg, 0.61 mmol) was added and the mixture stirred for 1 h at room temperature. Further N-bromosuccinimide (54 mg, 0.31 mmol) was added and the mixture stirred for 2.5 h. The mixture was diluted with DCM then washed with aqueous sodium bicarbonate, water, dried (Na$_2$SO$_4$), filtered and evaporated. The residue was purified by chromatography on a 5 g Si II column eluting with 1:2 ethyl acetate:DCM. Concentration of the appropriate fractions gave Intermediate 15G (137 mg, 64% yield).

LCMS (Method U2) Rt=1.37 min, m/z 443, 445 [M+Na]+

Intermediate 15H. (±)-5-(1-Hydroxy-ethyl)-1-methyl-3-oxo-2-(3-trifluoromethyl-phenyl)-2,3-dihydro-1H-pyrazole-4-carboxylic acid ethyl ester

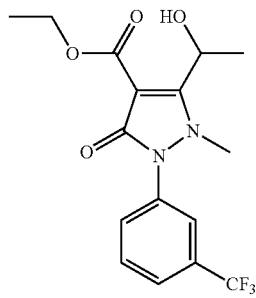 [SMILES: CCOC(=O)c1c(C(C)O)n(C)n(-c2cccc(C(F)(F)F)c2)c1=O]

A solution of Intermediate 15G (1.3 g, 3.1 mmol) was formed in acetonitrile (25 mL). Silver acetate (1.54 g, 9.26 mmol) and water (10 mL) were added. The mixture was stirred until all the solids had dissolved then heated at 80° C. for 4 h. Potassium carbonate (1.93 g, 14 mmol) was then added and the heating continued for 5 h. The reaction mixture was allowed to cool and then diluted with ethyl acetate and water. The mixture was filtered through Celite and the filtrate was extracted with ethyl acetate. The combined organic phases were washed with water, brine, dried (Na$_2$SO$_4$), filtered and evaporated giving Intermediate 15H as a pale yellow oil (0.83 mg, 75% yield).

LCMS (Method U2) Rt=1.13 min, m/z 359 [M+H]+

Intermediate 15I. 5-Acetyl-1-methyl-3-oxo-2-(3-trifluoromethyl-phenyl)-2,3-dihydro-1H-pyrazole-4-carboxylic acid ethyl ester

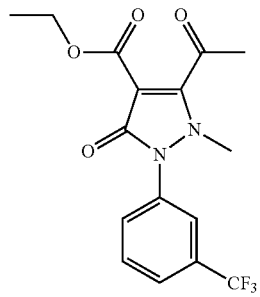 [SMILES: CCOC(=O)c1c(C(C)=O)n(C)n(-c2cccc(C(F)(F)F)c2)c1=O]

A solution of Intermediate 15H (0.83 g, 2.31 mmol) was formed in DCM (10 mL). Dess-Martin periodinane (1.18 g, 2.78 mmol) was added and the mixture stirred at room temperature for 2 h. The mixture was then diluted with DCM and filtered. The filtrate was washed with 10% potassium carbonate aqueous solution, water, brine, dried (Na$_2$SO$_4$), filtered and evaporated. The residue was purified by flash chromatography eluting with a gradient of 0%-50% ethyl acetate in DCM. Concentration of the appropriate fractions gave Intermediate 15I as a white solid (0.60 g, 73% yield).

LCMS (Method U2) Rt=1.19 min, m/z 357 [M+H]+

Intermediate 15J. 5-((E)-3-Dimethylamino-acryloyl)-1-methyl-3-oxo-2-(3-trifluoromethyl-phenyl)-2,3-dihydro-1H-pyrazole-4-carboxylic acid ethyl ester

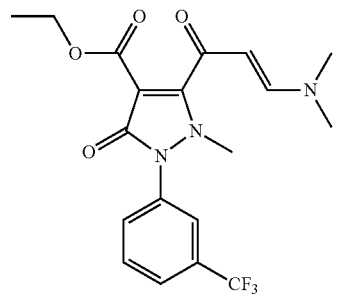 [SMILES: CCOC(=O)c1c(C(=O)/C=C/N(C)C)n(C)n(-c2cccc(C(F)(F)F)c2)c1=O]

Intermediate 15I (0.60 g, 1.68 mmol) was dissolved in Bredereck's reagent (3 mL). The mixture was heated at 90° C. for 30 minutes. The mixture was evaporated to give crude Intermediate 15J as a brown gummy solid (690 mg) used directly in the next reaction.

LCMS (Method U2) Rt=1.06 min, m/z 412 [M+H]+

Intermediate 15K. 2'-[4-Cyano-2-(2-dimethylamino-ethyl)-phenyl]-2-methyl-5-oxo-1-(3-trifluoromethyl-phenyl)-2,5-dihydro-1H,2'H-[3,3']bipyrazolyl-4-carboxylic acid ethyl ester

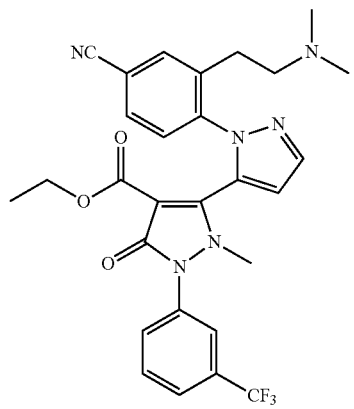 [SMILES: CCOC(=O)c1c(-c2ccnn2-c2ccc(C#N)cc2CCN(C)C)n(C)n(-c2cccc(C(F)(F)F)c2)c1=O]

A solution of Intermediate 15J (590 mg, 1.44 mmol) was formed in 2-propanol (10 mL). Concentrated HCl (0.6 mL) was added followed by Intermediate 9F (354 mg, 1.74 mmol). The mixture was heated at 85° C. for 4 h then the solvent was removed in vacuo. The residue was purified by flash chromatography eluting with a gradient of 0%-5% 2M NH$_3$/MeOH in DCM. Concentration of the appropriate fractions gave Intermediate 15K as a yellow foam (460 mg, 50% yield).

LCMS (Method U2) Rt=0.94 min, m/z 553 [M+H]+

Intermediate 15L. 2'-[4-Cyano-2-(2-dimethylamino-ethyl)-phenyl]-2-methyl-5-oxo-1-(3-trifluoromethyl-phenyl)-2,5-dihydro-1H,2'H-[3,3']bipyrazolyl-4-carboxylic acid cyclopentylamide

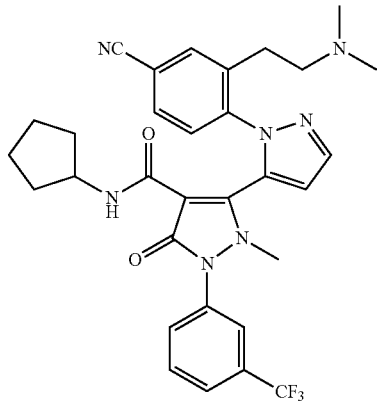 [SMILES: CN(C)CCc1cc(C#N)ccc1-n1nccc1-c1c(C(=O)NC2CCCC2)c(=O)n(-c2cccc(C(F)(F)F)c2)n1C]

Cyclopentyl amine (49 μL, 0.49 mmol) was added to a solution of bis(trimethylaluminum)-1,4-diazabicyclo[2.2.2]-octane (126 mg, 0.49 mmol) in THF (2.5 mL). The mixture was stirred in a sealed tube at 40° C. for 1 h. A solution of Intermediate 15K (180 mg, 0.32 mmol) in THF (2.5 mL) was added and the mixture stirred at 65° C. for 24 h then allowed to cool to room temperature. Diethyl ether was added followed by water (200 μL), 15% sodium hydroxide solution (200 μL) and water (500 μL). The mixture was then stirred for 30 minutes before sodium sulphate (solid) was added and the mixture was filtered and evaporated. The residue was purified by MDAP to give Intermediate 15L as a white solid (120 mg, 63% yield).

LCMS (Method U2) Rt=1.09 min, m/z 592 [M+H]+

(2-{5-Cyano-2-[4'-cyclopentylcarbamoyl-2'-methyl-5'-oxo-1'-(3-trifluoromethyl-phenyl)-2',5'-dihydro-1'H-[3,3']bipyrazolyl-2-yl]-phenyl}-ethyl)-trimethyl-ammonium benzene sulfonate A solution of Intermediate 15L (120 mg, 0.20 mmol) was formed in THF (2 mL). Methyl benzenesulfonate (40 μL, 0.3 mmol) was added and the mixture stirred at room temperature overnight. Diethyl ether was added and the white precipitate was washed by decantation using diethyl ether. The residual solid was then dried in vacuo to give the title compound as an off white solid (116 mg, 76% yield).

LCMS (Method 3): Rt=3.68 min, m/z 606.3 [M]+

$^1$H NMR (400 MHz, d6-DMSO): δ 8.11-8.05 (3H, m), 7.90-7.81 (3H, m), 7.76-7.72 (2H, m), 7.61-7.57 (2H, m), 7.38-7.27 (4H, m), 7.10 (1H, d, J=1.9 Hz), 3.94-3.86 (1H, m), 3.76-3.61 (2H, m), 3.31 (3H, s), 3.18-3.07 (2H, m), 3.11 (9H, s), 1.78-1.64 (2H, m), 1.59-1.46 (4H, m), 1.32-1.22 (1H, m), 1.15-1.07 (1H, m).

Example 16. Benzyl-(2-{5-cyano-2-[4'-cyclopentyl-carbamoyl-2'-methyl-5'-oxo-1'-(3-trifluoromethyl-phenyl)-2',5'-dihydro-1'H-[3,3']bipyrazolyl-2-yl]-phenyl}-ethyl)-dimethyl-ammonium bromide

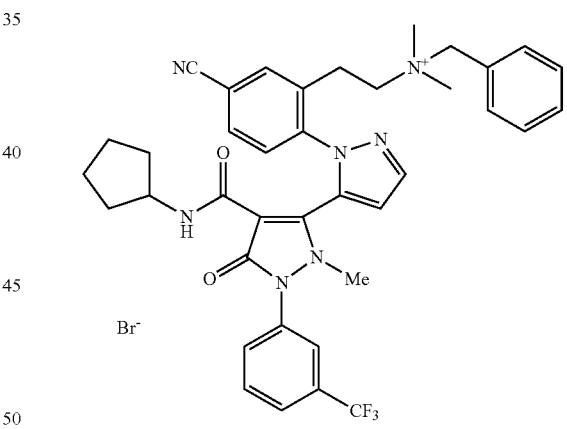

A solution of Intermediate 15L (45 mg, 0.08 mmol) was formed in THF (1 mL). Benzyl bromide (12 μL, 0.1 mmol) was added and the mixture stirred at room temperature overnight. Diethyl ether was added and the white precipitate was washed by decantation using diethyl ether. The residual solid was then dried in vacuo to give the title compound as an off white solid (45 mg, 78% yield).

LCMS (Method 3): Rt=4.06 min, m/z 682.4 [M]+

$^1$H NMR (400 MHz, d6-DMSO): δ 8.13 (1H, d, J=1.7 Hz), 8.09 (1H, d, J=7.1 Hz), 7.99 (1H, d, J=1.9 Hz), 7.91-7.82 (3H, m), 7.76-7.69 (2H, m), 7.61-7.49 (5H, m), 7.37 (1H, d, J=8.3 Hz), 7.10 (1H, d, J=1.9 Hz), 4.58 (2H, s), 3.91-3.82 (1H, m), 3.79-3.62 (2H, m), 3.29 (3H, s), 3.28-3.17 (2H, m), 3.02 (3H, s), 3.01 (3H, s), 1.77-1.61 (2H, m), 1.59-1.44 (4H, m), 1.31-1.22 (1H, m), 1.14-1.05 (1H, m).

Example 17. (2-{5-Cyano-2-[4'-cyclohexylcarbamoyl-2'-methyl-5'-oxo-1'-(3-trifluoromethyl-phenyl)-2',5'-dihydro-1'H-[3,3']bipyrazolyl-2-yl]-phenyl}-ethyl)-trimethyl-ammonium benzene sulfonate

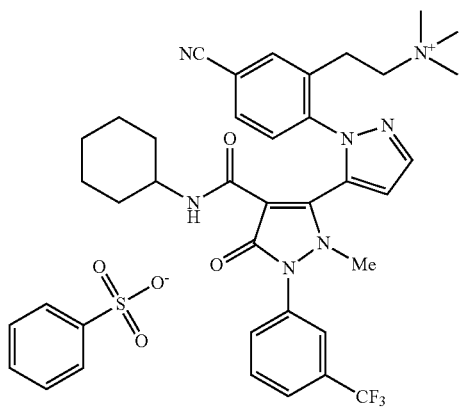 [SMILES: O=S(=O)([O-])c1ccccc1 ; Cn1c(-c2ccnn2-c2ccc(C#N)cc2CC[N+](C)(C)C)c(C(=O)NC2CCCCC2)c(=O)n1-c1cccc(C(F)(F)F)c1]

Intermediate 17A. 2'-[4-Cyano-2-(2-dimethylamino-ethyl)-phenyl]-2-methyl-5-oxo-1-(3-trifluoromethyl-phenyl)-2,5-dihydro-1H,2'H-[3,3']bipyrazolyl-4-carboxylic acid cyclohexylamide

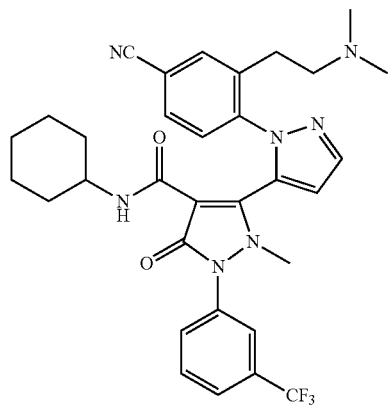 [SMILES: CN(C)CCc1cc(C#N)ccc1-n1nccc1-c1c(C(=O)NC2CCCCC2)c(=O)n(-c2cccc(C(F)(F)F)c2)n1C]

Intermediate 17A was synthesized using an analogous procedure to that for Intermediate 15L starting from Intermediate 15K (180 mg, 0.32 mmol) using cyclohexyl amine (56 μL, 0.49 mmol) to give Intermediate 17A (73 mg, 38% yield).

LCMS (Method U2) Rt=1.13 min, m/z 606 [M+H]+

(2-{5-Cyano-2-[4'-cyclohexylcarbamoyl-2'-methyl-5'-oxo-1'-(3-trifluoromethyl-phenyl)-2',5'-dihydro-1'H-[3,3']bipyrazolyl-2-yl]-phenyl}-ethyl)-trimethyl-ammonium benzene sulfonate A solution of Intermediate 17A (73 mg, 0.12 mmol) was formed in THF (2 mL). Methyl benzenesulfonate (24 μL, 0.18 mmol) was added and the mixture stirred at room temperature overnight. Diethyl ether was added and the white precipitate was washed by decantation using diethyl ether. The residual solid was then dried in vacuo to give the title compound as an off white solid (58 mg, 62% yield).

LCMS (Method 3): Rt=3.82 min, m/z 620.3 [M]+

$^1$H NMR (400 MHz, d6-DMSO): δ 8.14-8.05 (3H, m), 7.91-7.81 (3H, m), 7.78-7.93 (2H, m), 7.61-7.57 (2H, m), 7.38-7.27 (4H, m), 7.10 (1H, d, J=1.9 Hz), 3.77-3.59 (2H, m), 3.56-3.47 (1H, m), 3.31 (3H, s), 3.16-3.06 (2H, m), 3.11 (9H, s), 1.66-1.41 (5H, m), 1.32-1.00 (5H, m).

Biological Assay

Compounds of this invention were tested for potency in a human neutrophil elastase (HNE) enzyme activity assay.

HNE Enzyme Assay

Assays were performed in 96-well plates in a total assay volume of 100 μL. The final concentration of elastase enzyme (human leukocyte elastase, Sigma E8140) was 0.00072 U/mL. The peptide substrate (MeOSuc-Ala-Ala-Pro-Val-AMC, Calbiochem #324740) was used at a final concentration of 100 μM. The final concentration of DMSO was 1% in the assay buffer (0.05M Tris.HCl, 0.1M NaCl, 0.1M $CaCl_2$, 0.0005% brij-35, pH 7.5). The enzymatic reaction was started by addition of the enzyme and incubated at 25° C. for 30 minutes. After incubation, the reaction was stopped by addition of soybean trypsin inhibitor (Sigma T9003) at a final concentration of 50 μg/well. Fluorescence was measured using a Molecular Devices fluorescence plate reader using 380 nm excitation and 460 nm emission wavelengths.

A dose response to each compound was performed and the effect of compound in each experiment was expressed as a percentage inhibition of the control enzyme fluorescence. Dose response curves were plotted and compound potency ($IC_{50}$) was determined. Compounds were tested in at least two separate experiments. $IC_{50}$ values for tested Examples, representative of the invention, are shown in Table 1.

TABLE 1

| Example | HNE inhibition |
|---|---|
| 1, 2, 3, 4, 6, 7, 8, 9, 10, 11, 12, 13, 14, 15, 16, 17 | ++++ |
| 5 | +++ |

In the table above, HNE enzyme inhibition ($IC_{50}$ values) are indicated as follows:

1-10 nM '+++';

<1 nM '++++'.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

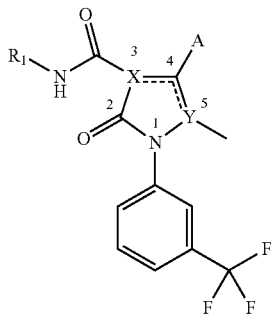

(I)

wherein
X is —C or —N;
Y is C or N, wherein X and Y are not simultaneously C or simultaneously N;
$R_1$ is linear or branched —$(C_1$-$C_6)$alkyl, —$(C_3$-$C_6)$cycloalkyl, —$(C_3$-$C_6)$heterocycloalkyl, or aryl$(C_1$-$C_6)$alkylene-, wherein any of said —$(C_3$-$C_6)$cycloalkyl, —$(C_3$-$C_6)$heterocycloalkyl, and aryl$(C_1$-$C_6)$alkylene- may be optionally substituted by linear or branched —$(C_1$-$C_6)$haloalkyl-C(O)—, —$(C_1$-$C_6)$alkylsulfonyl, or aryl$(C_1$-$C_6)$alkylene-OC(O)—;
A is a group of one of the following formulae:

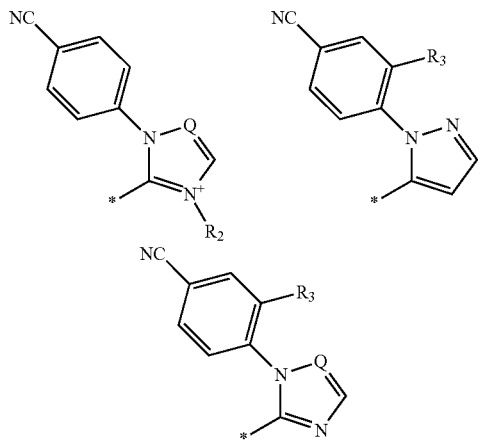

wherein
Q is —CH or N;
$R_2$ is —$(C_1$-$C_6)$alkyl, aryl$(C_1$-$C_6)$alkylene-, or heteroaryl$(C_1$-$C_6)$alkylene-;
$R_3$ is —$(C_1$-$C_6)$alkyleneN$^+$$R_a$$R_b$$R_c$ or heteroaryl$(C_1$-$C_6)$alkylene;
$R_a$ is —$(C_1$-$C_6)$alkyl;
$R_b$ is —$(C_1$-$C_6)$alkyl;
$R_c$ is —$(C_1$-$C_6)$alkyl, aryl-$(C_1$-$C_6)$alkylene, or heteroaryl$(C_1$-$C_6)$alkylene- or $R_a$ and $R_b$ together may form an heterocycloalkyl with the N$^+$ atom, wherein such heterocycloalkyl and heteroaryl may be optionally substituted by one or more $(C_1$-$C_6)$alkyl;
wherein the nitrogen atom in the heterocycloalkyl and heteroaryl groups may be quaternized; and
wherein the dotted lines connecting X to the carbon atom in position 4 and Y, indicate that when X is N, then the double bond is in 4-5 position, and when Y is N, then the double bond is in 3-4 position,
or a pharmaceutically acceptable salt thereof.
2. A compound or salt according to claim 1, wherein X is C and Y is N.
3. A compound or salt according to claim 1, wherein X is N and Y is C.
4. A compound or salt according to claim 1, wherein A is

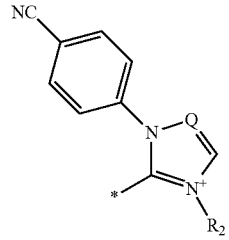

wherein Q is CH or N, and $R_2$ is —$(C_1$-$C_6)$alkyl or aryl$(C_1$-$C_6)$alkylene-.
5. A compound or salt according to claim 1, wherein A is

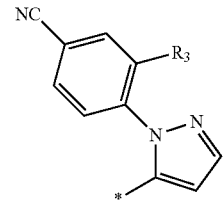

wherein $R_3$ is —$(C_1$-$C_6)$alkyleneN$^+$$R_a$$R_b$$R_c$, $R_a$ and $R_b$ are each independently —$(C_1$-$C_6)$alkyl; and $R_c$ is —$(C_1$-$C_6)$alkyl, aryl-$(C_1$-$C_6)$alkylene-, or heteroaryl$(C_1$-$C_6)$alkylene-.
6. A compound which is selected from the group consisting of:
1-(4-cyanophenyl)-2-{3-(cyclopentylcarbamoyl)-5-methyl-2-oxo-1-[3-(trifluoromethyl)phenyl]-2,3-dihydro-1H-imidazol-4-yl}-3-methyl-1H-imidazol-3-ium benzene sulfonate;
1-(4-cyanophenyl)-2-{3-(cyclopentylcarbamoyl)-5-methyl-2-oxo-1-[3-(trifluoromethyl)phenyl]-2,3-dihydro-1H-imidazol-4-yl}-3-benzyl-1H-imidazol-3-ium bromide;
1-(4-cyanophenyl)-2-{3-(cyclobutylcarbamoyl)-5-methyl-2-oxo-1-[3-(trifluoromethyl)phenyl]-2,3-dihydro-1H-imidazol-4-yl}-3-methyl-1H-imidazol-3-ium benzene sulfonate;
1-(4-cyanophenyl)-2-{3-[1-(2,2,2-trifluoro-acetyl)-piperidin-4-ylcarbamoyl]-5-methyl-2-oxo-1-[3-(trifluoromethyl)phenyl]-2,3-dihydro-1H-imidazol-4-yl}-3-methyl-1H-imidazol-3-ium benzene sulfonate;
1-(4-cyanophenyl)-2-{3-(4-methanesulfonyl-benzylcarbamoyl)-5-methyl-2-oxo-1-[3-(trifluoromethyl)phenyl]-2,3-dihydro-1H-imidazol-4-yl}-3-methyl-1H-imidazol-3-ium benzene sulfonate;
1-(4-cyano-phenyl)-5-[3-cyclopentylcarbamoyl-5-methyl-2-oxo-1-(3-trifluoromethyl-phenyl)-2,3-dihydro-1H-imidazol-4-yl]-4-methyl-1H-[1,2,4]triazol-4-ium benzene sulfonate;
3-(4-cyano-phenyl)-2-[4-cyclopentylcarbamoyl-2-methyl-5-oxo-1-(3-trifluoromethyl-phenyl)-2,5-dihydro-1H-pyrazol-3-yl]-1-methyl-3H-imidazol-1-ium benzenesulfonate;

1-(4-cyano-phenyl)-5-[4-cyclopentylcarbamoyl-2-methyl-5-oxo-1-(3-trifluoromethyl-phenyl)-2,5-dihydro-1H-pyrazol-3-yl]-4-methyl-1H-[1,2,4]triazol-4-ium benzenesulfonate;

[2-(5-cyano-2-{5-[3-cyclopentylcarbamoyl-5-methyl-2-oxo-1-(3-trifluoromethyl-phenyl)-2,3-dihydro-1H-imidazol-4-yl]-pyrazol-1-yl}-phenyl)-ethyl]-trimethyl-ammonium benzene sulfonate;

benzyl-[2-(5-cyano-2-{5-[3-cyclopentylcarbamoyl-5-methyl-2-oxo-1-(3-trifluoromethyl-phenyl)-2,3-dihydro-1H-imidazol-4-yl]-pyrazol-1-yl}-phenyl)-ethyl]-dimethyl-ammonium bromide;

[2-(5-cyano-2-{5-[3-cyclohexylcarbamoyl-5-methyl-2-oxo-1-(3-trifluoromethyl-phenyl)-2,3-dihydro-1H-imidazol-4-yl]-pyrazol-1-yl}-phenyl)-ethyl]-trimethyl-ammonium benzene sulphonate;

[2-(5-cyano-2-{5-[3-cyclopropylcarbamoyl-5-methyl-2-oxo-1-(3-trifluoromethyl-phenyl)-2,3-dihydro-1H-imidazol-4-yl]-pyrazol-1-yl}-phenyl)-ethyl]-trimethyl-ammonium benzene sulphonate;

[2-(5-cyano-2-{5-[3-ethylcarbamoyl-5-methyl-2-oxo-1-(3-trifluoromethyl-phenyl)-2,3-dihydro-1H-imidazol-4-yl]-pyrazol-1-yl}-phenyl)-ethyl]-trimethyl-ammonium benzene sulphonate;

[2-(5-cyano-2-{5-[3-isopropylcarbamoyl-5-methyl-2-oxo-1-(3-trifluoromethyl-phenyl)-2,3-dihydro-1H-imidazol-4-yl]-pyrazol-1-yl}-phenyl)-ethyl]-trimethyl-ammonium benzene sulphonate;

(2-{5-cyano-2-[4'-cyclopentylcarbamoyl-2'-methyl-5'-oxo-1'-(3-trifluoromethyl-phenyl)-2',5'-dihydro-1'H-[3,3']bipyrazolyl-2-yl]-phenyl}-ethyl)-trimethyl-ammonium benzene sulfonate;

benzyl-(2-{5-cyano-2-[4'-cyclopentylcarbamoyl-2'-methyl-5'-oxo-1'-(3-trifluoromethyl-phenyl)-2',5'-dihydro-1'H-[3,3']bipyrazolyl-2-yl]-phenyl}-ethyl)-dimethyl-ammonium bromide; and (2-{5-cyano-2-[4'-cyclohexylcarbamoyl-2'-methyl-5'-oxo-1'-(3-trifluoromethyl-phenyl)-2',5'-dihydro-1'H-[3,3']bipyrazolyl-2-yl]-phenyl}-ethyl)-trimethyl-ammonium benzene sulfonate, or a pharmaceutically acceptable salt of said compound.

7. A pharmaceutical composition, comprising a compound or salt according to claim 1 and a pharmaceutically acceptable carrier or excipient.

8. A pharmaceutical composition according to claim 7 which is in a form suitable for oral administration or administration by the pulmonary route.

9. A method for the treatment of a disease or condition in which HNE is implicated, comprising administering an effective amount of a compound or salt according to claim 1 to a subject in need thereof.

10. A method according to claim 9, wherein the disease or condition is chronic obstructive pulmonary disease, bronchiectasis, chronic bronchitis, lung fibrosis, pneumonia, acute respiratory distress syndrome, pulmonary emphysema, smoking-induced emphysema, or cystic fibrosis.

11. A method according to claim 9, wherein the disease or condition is asthma, rhinitis, psoriasis, atopic dermatitis, non-atopic dermatitis, Crohn's disease, ulcerative colitis, or irritable bowel disease.

\* \* \* \* \*